(12) United States Patent
Karp et al.

(10) Patent No.: US 10,568,840 B2
(45) Date of Patent: Feb. 25, 2020

(54) SELF ASSEMBLED GELS FOR CONTROLLED DELIVERY OF ENCAPSULATED AGENTS TO CARTILAGE

(71) Applicant: The Brigham and Women's Hospital, Inc., Boston, MA (US)

(72) Inventors: Jeffrey Karp, Brookline, MA (US); Nitin Joshi, Quincy, MA (US); Xueyin He, Ontario (CA); Sachin Bhagchandani, Cambridge, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 126 days.

(21) Appl. No.: 15/589,891

(22) Filed: May 8, 2017

(65) Prior Publication Data
US 2017/0319499 A1 Nov. 9, 2017

Related U.S. Application Data

(60) Provisional application No. 62/332,664, filed on May 6, 2016.

(51) Int. Cl.
*A61K 9/48* (2006.01)
*A61K 9/00* (2006.01)
(Continued)

(52) U.S. Cl.
CPC .......... *A61K 9/4833* (2013.01); *A61K 9/0019* (2013.01); *A61K 9/06* (2013.01);
(Continued)

(58) Field of Classification Search
CPC ......... A61K 47/14; A61K 9/0019; A61K 9/06
See application file for complete search history.

(56) References Cited

U.S. PATENT DOCUMENTS

| 5,603,959 A | 2/1997 | Horrobin |
| 6,031,017 A | 2/2000 | Waki |

(Continued)

FOREIGN PATENT DOCUMENTS

| EP | 1063007 | 12/2000 |
| EP | 0517211 | 9/2004 |

(Continued)

OTHER PUBLICATIONS

Valecillo, et al., "A liquid crystal of ascorbyl palmitate, used as vaccine platform, provides sustained release of antigen and has intrinsic pro-inflammatory and adjuvant activities which are dependent on My088 adaptor protein", Journal of Controlled Release, 214: 12-22 (2015).*

(Continued)

*Primary Examiner* — Kortney L. Klinkel
(74) *Attorney, Agent, or Firm* — Pabst Patent Group LLP

(57) ABSTRACT

A self-assembled gel composition with enhanced adhesion to cartilage tissue is provided. A cationic agent co-self assembles with a generally regarded as safe (GRAS), low molecular weight (<2,500 Da) gelator, forming homogeneous self-supporting gel that can encapsulate one or more therapeutic agents for controlled release. The composition adheres to connective tissue, e.g., cartilage, to a greater extent and a greater length of time than a self-assembled gel from gelators alone. The composition is used to specifically target connective tissue and deliver one or more therapeutic, prophylactic, or diagnostic agents for controlled release to improve dosing efficacy.

23 Claims, 8 Drawing Sheets

(51) Int. Cl.
| | |
|---|---|
| *A61K 9/06* | (2006.01) |
| *A61K 9/70* | (2006.01) |
| *A61K 9/50* | (2006.01) |
| *A61M 31/00* | (2006.01) |
| *A61K 31/7028* | (2006.01) |
| *A61K 31/7024* | (2006.01) |
| *A61K 47/14* | (2017.01) |
| *A61K 31/437* | (2006.01) |
| *A61K 31/495* | (2006.01) |
| *A61K 31/10* | (2006.01) |
| *A61K 31/245* | (2006.01) |
| *A61K 31/167* | (2006.01) |
| *A61K 31/40* | (2006.01) |
| *A61K 31/55* | (2006.01) |

(52) U.S. Cl.
CPC ............... *A61K 9/70* (2013.01); *A61K 31/10* (2013.01); *A61K 31/167* (2013.01); *A61K 31/245* (2013.01); *A61K 31/40* (2013.01); *A61K 31/437* (2013.01); *A61K 31/495* (2013.01); *A61K 31/55* (2013.01); *A61K 31/7024* (2013.01); *A61K 31/7028* (2013.01); *A61K 47/14* (2013.01); *A61K 9/5015* (2013.01); *A61M 31/002* (2013.01)

(56) References Cited

U.S. PATENT DOCUMENTS

| | | | |
|---|---|---|---|
| 6,471,970 | B1 | 10/2002 | Fanara |
| 7,749,485 | B2 | 7/2010 | Tournier |
| 2005/0084470 | A1 | 4/2005 | Abbas |
| 2005/0220822 | A1 | 10/2005 | Hoffman |
| 2005/0267036 | A1 | 12/2005 | Garry |
| 2005/0287198 | A1 | 12/2005 | Murthy |
| 2006/0276676 | A1 | 12/2006 | van Bommel |
| 2008/0004398 | A1 | 1/2008 | Durrieu |
| 2008/0038316 | A1 | 2/2008 | Wong |
| 2009/0110735 | A1 | 4/2009 | Maggio |
| 2009/0169498 | A1 | 7/2009 | de Jong |
| 2009/0263489 | A1 | 10/2009 | Zanella |
| 2010/0129451 | A1 | 5/2010 | John |
| 2012/0022158 | A1 | 1/2012 | Niu |
| 2012/0189588 | A1 | 7/2012 | Nahas |
| 2013/0273140 | A1 | 10/2013 | Maggio |
| 2013/0280334 | A1 | 10/2013 | Karp |
| 2013/0309286 | A1 | 11/2013 | Engstad |
| 2014/0302144 | A1 | 10/2014 | Koutsopoulos |
| 2015/0202586 | A1 | 7/2015 | Imoto |
| 2015/0297731 | A1 | 10/2015 | Chiou |
| 2016/0243026 | A1 | 8/2016 | Pathak |
| 2017/0000888 | A1 | 1/2017 | Karp |
| 2017/0319500 | A1 | 11/2017 | Karp |
| 2018/0050055 | A1 | 2/2018 | Ahmed |

FOREIGN PATENT DOCUMENTS

| | | |
|---|---|---|
| EP | 2361640 | 8/2011 |
| FR | 2417494 | 9/1979 |
| WO | 9907416 | 2/1999 |
| WO | 2006008386 | 1/2006 |
| WO | 2010033726 | 3/2010 |
| WO | 2012040623 | 3/2012 |
| WO | 2014089472 | 6/2014 |

OTHER PUBLICATIONS

Bennett, et al., "Next-generation hydrogel films as tissue sealants and adhesion barriers," Cardiac Surgery 18:494-9 (2003).
Bhattacharya, et al., "In Molecular Gels," Kluwer Academic Publishers: The Netherlands (2004).
Bhuniya, et al., "(S)-(+)-Ibuprofen-Based Hydrogelators: An Approach Toward Anti-Inflammatory Drug Delivery," Tetrahedron Lett. 47:7153-6 (2006).
Bong, et al., Angew. "Self-Assembling Organic Nanotubes," Chem. Int. 40:988-1011 (2001).
Bonte and Juliano, "Interactions of liposomes with serum proteins", Chem Phys Lipids, 40:359-72 (1986).
Boutaud, et al., J.A. "Determinants of the Cellular Specificity of Acetaminophen as an Inhibitor of Prostaglandin H(2) Synthases," PNAS, 99:7130-5 (2002).
Browne, et al., "Clinical outcome of autologous chondrocyte implantation at 5 years in US subjects", Clin Orthop Relat Res., 436:237-45 (2005).
Bryers, et al., "Biodegradtion of Poly(anhydride-esters) into Non-Steroidal Anti-Inflammatory Drugs and Their Effect on Pseudomonas aeruginosa Biofilms in Vitro and on the Foreign-Body Response In Vivo," Biomaterials, 27:5039-48 (2006).
Burns, et al., „Physical characterization and lipase suspectibility of short chain lecithin/triglycer mixed micelles potential lipoprotein models, J Biol Chem., 256(6):2716-22 (1981).
Casuso, et al., "Converting drugs into gelators: supramolecular hydrogels from N-acetyl-L-cysteine and coinage-metal salts", Org Biomol Chem., 8:5455-8 (2010).
Choi, et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", J Materials Sci., 12:67-73 (2001).
Chourasia, et al., "Pharmaceutical Approaches to Colon-Targeted Drug Delivery Systems," Pharm. Pharmaceut. Sci., 6:22-66 (2003).
Donati, et al.,"Synergistic effects im semidilute mixed solutions of alginate and lactose-midified chitosam (chitlac)", Biomacromolecules, 8:957-62 (2007).
Erdmann, et al., "Degradable Poly(anhydridie ester) Implants: Effects of Localized Salicylic Acid Release on Bone," Biomaterials, 21:2507-12 (2000).
Estroff, et al., "Effective Gelation of Water Using a Series of Bis-urea Dicarboxylic Acids," Angew. Chem. Int. Ed. 39:3447-50 (2000).
European Search Report for EP 11827647 dated Jul. 16, 2014.
Fischel-Ghodsian, et al., "Enzymatically Controlled Drug Delivery," PNAS. 85:2403-6 (1988).
Friggeri, et al., "Entrapment and release of quinoline derivatives using a hydrogel ofa low molecular weight gelator", Controlled Release 97: 241-8 (2004).
Gong, et al., "Synthesis ofhydrogels with extremely low surface friction", J. Am. Chem. Soc., 123:5582 (2001).
Gopinath, et al., "Ascorby1 palmitate vesicles (aspasomes): formation characterization and applications", Intl J Pharma., 271(1-2):95-113 (2004).
Gupta, et al., "Hydrogels.from controlled release to pH-responsive drug delivery", Drug Discovery Today, 7:569-79 (2002).
Han, et al., "Catalytic ester-amide exchange using group (iv) metal alkoxide-activator complexes", JACS, 127:10039-44 (2005).
Hans, et al., "Synthesis and characterization ofmPEG-PLA prodrug micelles", Biomacromolecules, 6, 2708-17 (2005).
Harten, et al., "Salicylic acid-derived poly(anhydride-esters) inhibit bone resorption and formation in vivo", Biomed. Mater. Res-A 72A:354-62 (2005).
Hoare, et al., Hydrogelsin drug delivery: Progress and challenges, Polymer, 49:1993-2007 (2008).
Huang, et al., "On the importance and mechanisms of burst release in matrix-controlled drug delivery systems", Controlled Release, 73: 121-36 (2001).
Hunziker, "Articular cartilage repair: basic science and clinical progress. A review of the current status and prospects", Osteoarthritis Cartilage, 10:432-63 (2002).
INDOMETHACIN, MSDS product information, copywright Jun. 19, 2012.
International Search Report for PCT/US2009/057349 dated May 6, 2009.
International Search Report for PCT/US2011/053075 dated Apr. 17, 2012.

(56) References Cited

OTHER PUBLICATIONS

International Search Report for PCT/US2016/031614 dated Jul. 26, 2017.
International Search Report for PCT/US2016/056070 dated Jan. 12, 2017.
International Search Report for PCT/US2017/031615 dated Sep. 25, 2017.
Jen, et al., "Review. Hydrogels for cell immobilization", Biotechnol. Bioeng.,50: 357-64 (1996).
John, et al., "Biorefinery. A design tool for molecular gelators," Langmuir. 26: 17843-51 (2010).
John, et al., "Enzymatically Derived Sugar-Containing Self-Assembled Organogels with Nanostructured Morphologies," Agnew. Chem. Int. Ed. 45:4772-5, 2006.
John, et al., "Lipid-based nanotubes asfunctional architectures with embedded fluorescence and recognition capabilities", J. Am. Chem. Soc., 126, 15012-13 (2004).
John, et al., "Morphological control of helical solid bilayers in high-axial-ratio nanostructures through binary sell-assemble", Chem. Eur. J., 8:5494-500 (2002).
John, et al., "Unsaturation effect on gelation behavior ofaryl glycolipids", Langmuir, 20:2060-5 (2004b).
John, et al.,"Nanotube Formation from Renewable Resources via Coiled Nanofibers", AdV. Mater., 13:715-18 (2001).
Jovanovic, et al., "How curcumin works preferentially with water soluble antioxidants", Chem. Soc., 123, 3064-68 (2001).
Jung, et al., "Self-Assembly ofa Sugar-Based Gelator in Water. Its Remarkable Divers ity in Gelation Ability and Aggregate Structure," Lanumuir 17, 7229-32 (2001).
Kalgutkar, et al., "Ester and Amide Derivatives of the Nonsteriodal Antiinflammatory Drug,Indomethacin, as selective cyclooxygenase-2 inhibitors," J. Med. Chem.,43:2860-70 (2000).
Kamath, et al., "Biodegradable Hydrogels in Drug Delivery," Adv. Drug Deliv. Rev., 11:59-84 (1993).
Kim, et al., "In vivo evaluation of polymeric micellar paclitaxel formulation. toxicity and efficacy", Controlled Release, 72: 191-202 (2001).
Kitagawa, et al., "Cationic Vesicles Consisting of 1,2-Dioleoyl-3-Trimethylammonium Propane (DOTAP) and Phosphatidylcholines and Their Interaction with Erythrocyte Membrane", Chem Pharma Bull., 52(4):451-3 (2004).
Kiyonaka, et al., Semi-wc/ peptide/protein array using supramolecular hydrogel, Nat. Mater., 3,58-64 (2004).
Kobayashi, et al., "Molecular design of"super" hydrogelators. understanding the gelation process of azobenzene-based sugar derivatives in water", Org. Lett. 4: 1423-6 (2002).
Krog and Sparse,"Food emulsifiers: their chemical and physical properties", Food Emulsions,Fourth Ed., pp. 45FF, CRC Press (2004).
Kumar, et al., "Prodrugs as self-assembled hydrogels: a new paradigm for biomaterials", Biotech., 24:1-9 (2013.
Kumar, et al., "First snapshot o fa nonpolymeric hydrogelator interacting with its getting solvents", Chem. Commun., 4059-62 (2005).
Lee, et al., "Hydrogelsfor Tissue Engineering," Chem. Rev., 101: 1869-80 (2001).
Li, et al., „Molecular nanofibers of olsalazine form supramolecular hydrogeis for reductive release of an anti-inflammatory agent, JACS, 132:17707-9 (2010).
Loos, et al., "Design and Application of Self-Assembled Low Molecular Weight Hydrogels," Eur. J.Organic Chem. 17:3615-31 (2005).
Lu, et al., "Photopolymerization ofmultilaminated poly(HEMA) hydrogels for controlled release", Controlled Release, 57:291-300 (1999).
Luboradzki, et al., "AnAttempt to Predict the Gelation Ability ofHydrogen-Bond-Based Gelators Utilizing a Glvcosidase Librarv," Tetrahedron 56:9595-9 (2000).

Magnussen, et al., "Treatment of focal articular cartilage defects in the knee: a systematic review", Clin Orthop Relat Res, 466:952-96 (2008).
Makarevic, et al., "Bis(amino acid) oxalyl amides as ambidextrous gelators of water and organicsolvents. supramolecular gels with temperature dependent assembly/ dissolution equilibrium",Chem. Eur. J. 7:3328-41 (2001).
Marsich, et al., "Alginate/lactose-modified chitosan hydrogels: A bioactive biomaterial for chondrocyte encapsulation", J Biomat Mater Res A, 84(2):364-76 (2008).
Mazumdar, et al., "Preparation and evalulation ofethambutol derivatives," Indian J. Pharm. Sci., 47: 179-80 (1985).
Menger, et al., "Anatomy ofa Gel. Amino Acid Derivatives that Rigidify Water at Submillimolar Concentrations," J. Am. Chem. Soc. 122:11679-91 (2000).
Miyata, et al., "Biomolecule-Sensitive ydrogels," Adv. Drug Deliv. Rev., 54:79-98 (2002).
Moliner, et al., "PFGSE-NMR study of the self-diffusiom of sucrose fatty acid monoesters in water", J Colloid Interface Sci., 286(1):360-8 (2005).
Nicolaou, et al., "A Water-Soluble Prodrug of Taxol with Self-Assembling Properties," Agew.Chem. Int. Ed., 33: 1583-7 (1994).
Nishimura, et al., "Analysis of reducing end-groups produced by enzymatic scission of glycoside linkages in O-methylcellulose", Carbohydrate Res., 267:291-8 (1995).
Oda, et al., "Gemini Surfactants as New, Low Molecular Weight Gelators of Organic Solvents and Water," Angew. Chem. Int. Ed. 37, 2689-91 (1998).
Palma, et al., „Evaluation of the surfactant properties of ascorbyl palmitage sodium salt, Eu J Pharma Sci., 16(1-2):37-43 (2002).
Peppas, "Hydrogels and Drug Delivery," Curr. Opin. Colloid Interface Sci. 2:531-7 (1997).
Peppas, et al., "Hydrogels in Biology and Medicine. From Molecular Principles to Bionanotechnologv," R. Adv. Mater., 18:1345-60 (2006).
Peppas, et al., "Hydrogels in pharmaceutical formulations," Eur. J. Pharm. Biopharm., 50:27-46 (2000).
Persico, et al.,"Effect of tolmetin glycine amide (McN-4366) a prodrug of tolmetin sodkum on adjuvant arthritis in the rat", J Pharma Exp Therap., 247(3):889-96 (1988).
Pietzyk, et al., "Degradation of phosphatidylcholine in liposomes containing carboplatin in dependence on composition and storage conditions", Intl J Pharma., 196(2):215-8 (2008).
Poulsen, et al., "Effect of topical vehicle composition on the in vitro release of fluocinolone acetonide and its acetate ester", J Pharma Sci., 57(6):928-33 (1968).
Preliminary Report on Patentability for PCT/US2011/053075 dated Mar. 26, 2013.
Qiu, et al., "Environment-sensitive hydrogels for drug dc/ivory,"Adv. Drug Deliv. Rev., 53, 321-39 (2001).
Rajabalaya, et al., "Studies on effect of plasticizer on invitro release and exvivo permeation from eudragit e100 based chlorpheniramine maleate matrix type transdermal delivery system", J Excipients Food Chem., 1(2):1-12 (2010).
Rattie, et al., "Acetaminophen Prodrugs III. Hydrolysis of Carbonate and Carboxylic Acid Esters in Aqueous Bu[[ers," J. Pharm. Sci., 59: 1738-41 (1970).
Robinson, et al., "Design, synthesis, and biological evaluation ofangiogenesis inhibitors. Aromatic cnonc and dienone analogues ofcurcumin", Bioru. Med. Chem. Lett., 13:115-17 (2003).
Rooseboom, et al., "Enzyme-catalyzed activation ofanticancer prodrugs", Pharmacol. Rev., 56:53-102 (2004).
Scogs, substances list, http://www.fda.gov/Food/IngredientsPackagingLabeling/GRAS/SCOGS/ucm084104. Retrieved from interner Apr. 3, 2014.
Sinha, et al., "Microbially triggered drug delivery to the colon", Eur. J. Pharm. ScL, 18:3-18 (2003).
Sreenivasachary, et al., "Gelation-driven component selection in the generation of constitutional dynamic hydrogels based on guanine-quartet formation", PNAS, 102:5938-43 (2005).
Szuts, et al., „Study of thermo-sensitive gel-forming properties of sucrose stearates, J Excipients Food Chem., 1(2):13-20 (2010).

(56) References Cited

OTHER PUBLICATIONS

Tomsic, et al., "Internally self-assembled thermoreversible gelling mulsions:ISAsomes in methylcellulose, k-carragrrnan, and mixed hydrogels", Langmuir, 25:9525 (2009).
Toth and Urtis, "Commonly used muscle relaxant therapies for acute low back pain: A review of carisoprodol cyclobenzaprine hydrochloride, and metaxalone", Clin Therap., 26(9):1355-67 (2004).
Trouet, et al., "Extracellularly tumor-activated prodrugs for the selective chemotherapy of cancer application to doxorubicin and preliminary in vitro and in vivo studies", Cancer Res., 61: 2843-6 (2001).
Troung, et al., "Self assembled gels for biomedical applications", Focus Rev., 6:30-42 (2011).
Ullrich, et al.. "Sucrose ester nanodispersions: microciscosity and viscoelastic properties", Eu J Pharma Biopharma, 70:550-5 (2008).
Van Bommel, et al., "Two-stage enzyme mediated drug release from LMWG gydrogels," Org.Biomol. Chem. 3:2917-20 (2005).
van der Linden, et al., "Clinic/us-scnsi/ivc hydrogels and their applications in chemical (micro)analvsis", Analyst, 128:325-31 (2003).
Van Esch, et al., "New functional materials based om self-assembling organogels: from serendipity towards design", Angew Chem Int., 39:2263-66 (2000).
Vassilev, et al., "Enzymatic Synthesis of a Chiral Gelator with Remarkably Low Molecular Weight,"Chem. Commun., 1865-6 (1998).
Vemula, et al., "Encyme Catalysis. Tool to Make and Break Amygdalin Hydrogelators from Renewable Resources. A Delivery Model for Hydrophobic Drugs", J. Am. Chem. Soc., 128: 8932-8 (2006).
Vemula, et al., "In Situ Synthesis of Gold Nanoparticles using Molecular Gels and Liquid Crystals from Vitamin-C Amphiphiles," Chem. Mater. 19, 138-40 (2007).
Vemula, et al., "Smart Amphiphiles. Hydro/Organogelators for In Situ Reduction of Gold", Chem.Commun., 2218-20 (2006).
Vigroux, et al., "Cyclization-activated prodrugs: N-(substituted 2-hydroxyphenyl and 2-hydroxypropyl)carbamates based on ring-opened derivatives of active benzoxazolones and oxazolidinones as mutual prodrugs of acetaminophen", J Med Chem., 38:3983-94 (1995).
Vohra, et al., "Nanolipi carrier-based thermoreversible gel for localized delivery of docetaxel to breast cancer", Cancer Nanotechnol., 4(1-3):1-12 (2013).

Wang, et al., "Low Molecular Weight Organogelators for Water," Chem. Commun. 310-11 (2003).
Wang, et al., "Hydrogels as separation agents responsive gels", Transitions II, Adv Polymer Sci., 110:67-79 (1993).
Whitesides, et al., "Beyond molecules. self-assembly ofmesoscopic and macroscopic components", PNAS, 4769-74 (2002).
Xing, et al., J. "Hydrophobic Interaction and Hydrogen Bonding Cooperatively Confer a Vancomycin Hydrogel. A Potential Candidatefor Biomaterials," J. Am. Chem. Soc. 124:14846-7 (2002).
Yan, et al., "Enzymatic Production ofsugar Fatty Acids Esters," PhD thesis, University of Stuttgard, (2001).
Yang, et al., "A Simple Visual Assay Based on Small Molecule Hydrogels for Detecting Inhibitors of Prcrmcs," Chem. Commun., 2424-5 (2004).
Yang, et al., "Enzymatic Formation of Supramolecular Hydrogels," Adv. Mater., 16:1440-4 (2004b).
Yang, et al., "Enzymatic Hydrogelation ofsmall Molecules", Ace. Chem. Res., 41:315-26 (2008).
Yang, et al., "Small Molecular Hydrogels Based on a Class ofAnti-Inflammatory Agents," Chem. Commun., 208-9 (2004c).
Yang, et al., "Using a Kinase/Phosphatase Switch to Regulate a Supramolecular Hydrogel and Forming the Supramolecular Hvdrogel In Vivo," J. Am. Chem. Soc. 128:3038-43 (2006).
Zhang, et al., "An inflammation-targeting hydrogel for local drug delivery in inflammatory bowel disease", Sci Transl Med., 7(300):300ra128 (2015).
Zhang, et al., "Hydrogels: Wet or Let Die," Nature Materials 3:7-8 (2004).
Zhang, et al., "Self-assembled networks and molecular gels derived fro, long-chain, naturally-occurring fatty acids", J Brazilian Chem Soc., 239-55 (2016).
Zhang, et al., "Versatile small-moleule motifs for self-assemly in water and the formation of viofunctional supramolecular hydrogels", Langmuir, 27(2):529-37 (2011).
Higuchi, et al. Specificity of Esterases and Effect of Structure of Prodrug Esters of Acylated Acetaminophen on Hyrdolic Reacitvity in Pharmacokinetics (1984).
International Search Report PCTUS2019/025782 dated Jun. 26, 2019.
Thoughco., "Phosphate-Buffered Saline or PBS SOlution", https://www.thoghtco.com/phophate-buffered-saline-pbs-solution-4061933 (2018).

* cited by examiner

SELF ASSEMBLED GELS FOR CONTROLLED DELIVERY OF ENCAPSULATED AGENTS TO CARTILAGE

CROSS-REFERENCE TO RELATED APPLICATIONS

This application claims benefit of and priority to U.S. Provisional Application No. 62/332,664, filed on May 6, 2016, which is hereby incorporated herein by reference in its entirety.

STATEMENT REGARDING FEDERALLY SPONSORED RESEARCH OR DEVELOPMENT

This invention was made with government support under Grant No. AR063866 awarded by the National Institutes of Health and Grant No. W81XWH-14-1-0229 awarded by the Army. The government has certain rights in the invention.

FIELD OF THE INVENTION

The disclosed technology is generally in the field of controlled delivery of drug, and more particularly, relates to injectable adhesive hydrogel for cartilage repair.

BACKGROUND OF THE INVENTION

Cartilage (hyaline cartilage or articular cartilage) is a 3-5 mm thin tissue that coats the boney surfaces inside joints, as well as forms other lubricating strong surfaces. It provides a very low friction articulation that ideally lasts a life time. Cartilage may be damaged through acute injury or degeneration over time. For example, osteoarthritis (OA) is a joint disorder that leads to thinning of cartilage and progressive joint damage. Nearly 40 percent of Americans over the age of 45 have some degree of knee OA, and those numbers are expected to grow as the population ages. Focal lesions of articular cartilage can progress to more widespread cartilage destruction and arthritis that is disabling. Articular cartilage has a limited intrinsic ability to heal. For this reason, orthopedic management of these lesions remains a persistent problem for the orthopedist and patient. The importance of treating injury to cartilage is underscored by the fact that several million people are affected in the United States alone by cartilage damage (Praemer A, et al. *American Academy of Orthopaedic Surgeons* 1999 p. 34-9).

Depending on the size and location of a cartilage defect, various surgical procedures are performed for cartilage repair including debridement, abrasion arthroplasty, microfracture, osteochondral autograft transfer, osteochondral allograft transplantation, and autologous chondrocyte implantation (Browne J E, et al. *Clinical Orthopaedics and Related Research* 2005; 436:237-245; Magnussen R A, et al. *Clinical Orthopaedics and Related Research* 2008; 466:952-96).

However, restoring a normal cartilaginous surface and improving integration with surrounding normal articular cartilage are highly challenging. Studies have shown implanting fully functional cartilage into defects, such as osteochondral auto- and allografts, often results in poor integration to the surrounding cartilage tissue (Hunziker E B. *Osteoarthritis Cartilage*. 2002; 10:432-463). Previous biomaterial implants have not succeeded in clinical and preclinical studies, owing to poor integration and the promotion of bone and fibrous tissue growth instead of hyaline cartilage, as is often seen with rigid materials in vivo (Custers R J, et al. *J Bone Joint Surg Am.* 2009; 91:900-910.).

Therefore, it is an object of the present invention to provide a biocompatible gel composition for good adhesion and integration with cartilage tissue and controlled delivery of therapeutic agents.

It is another object of the present invention to provide a method of treating and preventing cartilage damage.

SUMMARY OF THE INVENTION

A self-assembled gel composition with enhanced adhesion to cartilage tissue is provided. The gel composition can be a hydrogel or organogel, depending on the major solvent component using to form the gel, or which is present after solvent removal and/or purification. Preferably, self-assembled hydrogel is prepared from the co-self assembly of a low molecular weight, generally recognized as safe (GRAS) amphiphile gelator of less than 2,500 Da and a cationic agent that imparts adhesion capability to connective tissue, optionally encapsulating one or more therapeutic, prophylactic, and diagnostic agents, in an aqueous or substantially aqueous medium. Alternatively, a cationic agent may interact or associate with the GRAS amphiphile gelator, or coat the assembled gel formed from the GRAS amphiphile gelator, to impart cartilage adhesion and targeting capability.

In a first embodiment, a GRAS amphiphile gelator, a cationic agent to impart cartilage adhesion capability, and optionally therapeutic, prophylactic, and/or diagnostic agent, are dissolved in a co-solvent medium including both water (or an aqueous buffer or salt solution) and a water-miscible organic solvent, by mixing and optionally heating to insure complete dissolution. In a second embodiment, the GRAS amphiphile gelator is dissolved initially in an organic solvent to form a solution with the gelators as the solutes (termed "gelator solution"). A cationic agent to impart cartilage adhesion capability and optionally therapeutic agent, prophylactic, and/or diagnostic agent are also dissolved in the gelator solution. An aqueous solution such as pure water or an aqueous buffer or salt solution, optionally containing therapeutic agent, prophylactic, and/or diagnostic agent, is then mixed with the gelator solution to form a liquid gel solution. In either embodiment, heating the gel solution to a temperature (generally lower than the boiling point of any of the used liquid solvent) for a sufficient time, followed by cooling, results in a viscous homogeneous gel stable to inversion at room temperature (about ° C.) or body temperature (about °37).

Complete dissolution of components are critical to forming self-supporting (e.g., flow resisting especially when inverted) homogeneous gel, which is unlike heterogeneous gelation (e.g., clumps of gel in a mixture with non-gelled portion, or precipitates). Solvent(s), pH, and/or salt are selected to be effective to dissolve components into a homogeneous solution. Following formation of gel, excess solvent is removed to generate pharmaceutically acceptable hydrogel.

Suitable gelating amphiphilic compounds generally recognized as safe (GRAS) by the U.S. Food and Drug Administration. Exemplary gelators are enzyme-cleavable, generally recognized as safe (GRAS) compounds, such as ascorbyl alkanoate, sorbitan alkanoate, triglycerol monoalkanoate, sucrose alkanoate, glycocholic acid, and combinations thereof. To form a homogeneous self-supporting gel, the GRAS amphiphile gelators are usually included at greater than 3, 4, 5, 6, 7, 8, 9, or 10 wt/vol % in a liquid medium for gelation.

Cationic agents generally electrostatically interact with one or more components of cartilage and enhance adhesion of the viscous homogeneous gel to the cartilage, compared to control gel lacking the cationic agent. The cationic agents co-self assemble with the gelators, i.e., forming the lamellar, vesicular, or nanofibrous microstructures of the homogeneous gel. Suitable cationic agents include amine-containing phospholipids such as 1,2-dioleoyl-3-trimethylammonium propane (DOTAP) and 1,2-dioleyloxy-3-trimethylammonium propane chloride (DOTMA), as well as positively charged biocompatible molecules such as chitosan, carboxymethyl chitosan, and other derivatives of chitosan. To impart adhesion capability to connective tissue, the cationic agent is generally greater than 10, 11, 12, 13, 14, 15, 20, or 25% by weight in the combined mass containing a GRAS amphiphile gelator and the cationic agent. The mass ratio of the cationic agent to the GRAS amphiphile gelator is preferably at least 1:9 or greater than 1:9, e.g., 1.5:8.5, 2:8, 2.5:7.5, 3:7, or greater.

The self-assembled gel composition adheres to connective tissue such as cartilage, and can function as a lubricant and for controlled delivery of therapeutic agents. The self-assembled gel composition typically does not have a burst release of encapsulated agents when incubated in a liquid medium. For example, less than 10, 15, 20, 25, or 30% of the total amount of loaded drug is released from the viscous homogeneous gel when incubated in phosphate buffered saline at 37° C. for at least 1 week, 2 weeks, 3 weeks, 1 month, 2 months, or longer.

The self-assembled gel composition is administered to treat or prevent one or more cartilage damages. A common route of administration is via local injection, arthroscopically, or at the time of surgery.

BRIEF DESCRIPTION OF THE DRAWINGS

FIG. 9 compares triglycerol monostearate (TG18)-DOTAP co-assembled gel with TG18-only gel.

FIG. 10 compares sucrose palmitate (SP)-DOTAP co-assembled gel with SP-only gel.

FIG. 11 compares sucrose stearate (SS)-DOTAP co-assembled gel with SS-only gel.

DETAILED DESCRIPTION OF THE INVENTION

I. Definitions

Figure 1:
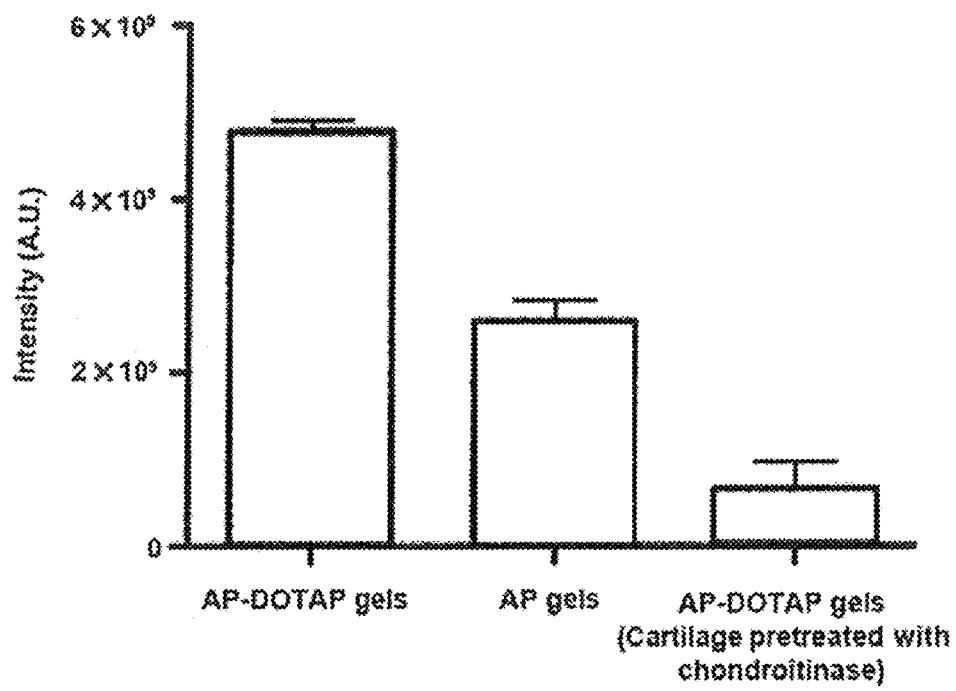
FIG. 1 is a bar graph showing the fluorescence intensity (arbitrary unit, A.U.) of cartilage explants following a 1-hour incubation with gels loaded with a fluorescent dye. AP-DOTAP gels refer to co-self assembled gel between ascorbyl palmitate and 1,2-dioleoyl-3-trimethylammonium propane. AP gels refer to self-assembled ascorbyl palmitate gel.

The term "gelators" refer to molecules that can assemble through non-covalent interactions, such as hydrogen-bonding, van der Waals interactions, hydrophobic interactions, ionic interactions, pi-pi stacking, or combinations thereof, in one or more solvents. The gelators can form a gel by rigidifying the solvent through, for example, capillary forces. Gelators can include hydrogelators (e.g., gelators that form hydrogels) and organo-gelators (e.g., gelators that form organo-gels). In some embodiments, gelators can form both hydrogels and organo-gels. Gelators include low molecular weight (<2,500 Da) generally recognized as safe amphiphilic compounds, optionally enzyme cleavable, which may independently self-assemble to form gel. A cationic agent that co-assembles with the amphiphile gelator to form co-self assembled gels can also be a co-gelator.

The term "self-assembling" refers to the capability of molecules to spontaneously assemble, or organize, to form a high ordered structure such as hydrogel or organo-gel in a suitable environment.

The term "hydrogel" refers to three-dimensional (3-D) networks of molecules covalently (e.g., polymeric hydrogels) or non-covalently (e.g., self-assembled hydrogels) held together where water is the major component. Gels form via self-assembly of gelators or via chemical crosslinking of gelators.

The term "organo-gel" refers to 3-D networks of molecules covalently (e.g., polymeric hydrogels) or non-covalently (e.g., self-assembled hydrogels) held together where an organic solvent is the major component. Gels can be formed via self-assembly of gelators or via chemical crosslinking of gelators.

The term "organic solvent" refers to any carbon-containing substance that, in its liquid phase, is capable of dissolving a solid substance. Exemplary organic solvents commonly used in organic chemistry include toluene, tetrahydrofuran, acetone, dichloromethane, and hexane. This term also includes polyethylene glycol (PEG), which can be melted at 37° C. for 1 kDa MW and potentially dissolve polar compounds.

The term "water-miscible" refers to any solvent that mixes with water, in all proportions, to form a single homogenous liquid phase. This includes solvents like dimethyl sulfoxide (DMSO), tetrahydrofuran, acetone, ethanol, methanol, and dioxane, but generally excludes solvents such as hexane, oils, and ether. It also excludes solvents that have some, very limited miscibility or solubility in water such as ethyl acetate and dichloromethane, which are practically considered immiscible. Generally between about 20% and 50% by volume of a water-miscible organic solvent is used to make the hydrogels, with the balance being water or a buffer.

The term "adhere" refers to a gel composition sticks to a surface or substance following contact or incubation for some time. A mild wash solution generally does not remove the adhered gel composition from the surface. This mild wash solution includes the solvent or medium in which the gel composition is formed. For comparative purpose chondroitinase treatment will reduce adhesion of a self-assembled gel including GRAS amphiphile gelators and cationic agents to cartilage.

The term "pharmaceutically acceptable," refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the U.S. Food and Drug Administration.

The terms "biocompatible" and "biologically compatible," as used herein, generally refer to materials that are, along with any metabolites or degradation products thereof, generally non-toxic to the recipient, and do not cause any significant adverse effects to the recipient. Biocompatible materials generally are materials which do not elicit a significant inflammatory or immune response when administered to a patient.

The term "molecular weight," as used herein, generally refers to the relative average chain length of the bulk polymer, unless otherwise specified. In practice, molecular weight is estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

The term "hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wettable by water.

The term "hydrophobic," as used herein, refers to the property of lacking affinity for or repelling water. For example, the more hydrophobic a polymer (or polymer segment), the more that polymer (or polymer segment) tends to not dissolve in, not mix with, or not be wetted by water.

The term "surfactant" as used herein refers to an agent that lowers the surface tension of a liquid.

The term "therapeutic agent" refers to an agent that can be administered to prevent or treat one or more symptoms of a disease or disorder. Therapeutic agents can be nucleic acids or analogs thereof, a small molecule (mw less than 2000 Daltons, more typically less than 1000 Daltons), peptidomimetic, protein, or peptide, carbohydrate or sugar, lipid, or a combination thereof. In some embodiments, cells or cellular materials may be used as therapeutic agents.

The term "chondrocytes" can mean, but is not limited to, cells found in cartilage that produce and maintain the cartilaginous matrix, as well as cells that differentiate to form cartilage. From least to terminally differentiated, the chondrocytic lineage is (i) colony-forming unit-fibroblast (CFU-F); (ii) mesenchymal stem cell/marrow stromal cell (MSC); (3) chondrocyte. The term "chondrogenesis" refers to the formation of new cartilage from cartilage forming or chondrocompetent cells.

The term "treating" or "preventing" a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "therapeutically effective amount" refers to an amount of the therapeutic agent that, when incorporated into and/or onto the self-assembled gel composition, produces some desired effect at a reasonable benefit/risk ratio applicable to any treatment. The effective amount may vary depending on such factors as the disease or condition being treated, the particular formulation being administered, the size of the subject, or the severity of the disease or condition.

The terms "incorporated" and "encapsulated" refers to incorporating, formulating, or otherwise including an agent into and/or onto a composition, regardless of the manner by which the agent or other material is incorporated.

II. Composition

1. GRAS Amphiphile Gelator

GRAS amphiphilic gelators suitable for self-assembly to form gel are generally less than 2,500 Da, and may preferably be enzyme-cleavable. The GRAS amphiphile gelators can self-assemble into gels based micro-/nano-structures (e.g., lamellar, micellar, vesicular, or fibrous structures).

In some embodiments, the GRAS amphiphile gelators are ascorbyl alkanoate, sorbitan alkanoate, triglycerol monoalkanoate, sucrose alkanoate, glycocholic acid, or any combination thereof.

The alkanoate can include a hydrophobic $C_1$-$C_{22}$ alkyl (e.g., acetyl, ethyl, propyl, butyl, pentyl, caprylyl, capryl, lauryl, myristyl, palmityl, stearyl, arachidyl, or behenyl) bonded via a labile linkage (e.g., an ester, a carbamate, a thioester and an amide linkage) to an ascorbyl, sorbitan, triglycerol, or sucrose molecule. For example, the ascorbyl alkanoate can include ascorbyl palmitate, ascorbyl decanoate, ascorbyl laurate, ascorbyl caprylate, ascorbyl myristate, ascorbyl oleate, or any combination thereof. The sorbitan alkanoate can include sorbitan monostearate, sorbitan decanoate, sorbitan laurate, sorbitan caprylate, sorbitan myristate, sorbitan oleate, or any combination thereof. The triglycerol monoalkanoate can include triglycerol monopalmitate, triglycerol monodecanoate, triglycerol monolaurate, triglycerol monocaprylate, triglycerol monomyristate, triglycerol monostearate, triglycerol monooleate, or any combination thereof. The sucrose alkanoate can include sucrose palmitate, sucrose decanoate, sucrose laurate, sucrose caprylate, sucrose myristate, sucrose oleate, or any combination thereof.

In some embodiments, the GRAS amphiphile gelators include ascorbyl palmitate, sorbitan monostearate, triglycerol monopalmitate, sucrose palmitate, or glycocholic acid.

Representative low molecular weight GRAS amphiphile gelators include vitamin precursors such as ascorbyl palmitate (vitamin C precursor), retinyl acetate (vitamin A precursor), and alpha-tocopherol acetate (vitamin E precursor).

In some forms, a GRAS amphiphile gelator is formed by synthetically conjugating one or more saturated or unsaturated hydrocarbon chains having $C_1$ to $C_{30}$ groups with a low molecular weight, generally hydrophilic compound, through esterification or a carbamate, anhydride, and/or amide linkage. The range $C_1$ to $C_{30}$ includes $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ etc. up to $C_{30}$ as wells as ranges falling within $C_1$ to $C_{30}$, for example, $C_1$ to $C_{29}$, $C_2$ to $C_{30}$, $C_3$ to $C_{28}$, etc.

In some embodiments, alpha tocopherol acetate, retinyl acetate, retinyl palmitate, or a combination thereof, can co-assemble with the gelators.

The gels can include, independently, from about three to a maximum of 30-40 percent, more preferably about 4% to 10% by weight gelator per volume of gel. Above 30-40% the gel will begin to precipitate out of solution or become less injectable.

In some forms, the self-assembled gel compositions include an enzyme-cleavable, generally recognized as safe (GRAS) first gelator having a molecular weight of 2500 or less and a non-independent second gelator that is also a GRAS agent. Non-independent gelators do not form self-support gel at the concentration that would typically form self-supporting gel if combined with an enzyme-cleavable GRAS gelator. Exemplary non-independent second gelators include alpha tocopherol acetate, retinyl acetate, and retinyl palmitate. The non-independent gelators co-assemble with the GRAS first gelators to form the self-assembled gels.

2. Cationic Agent

One or more cationic agents are included to co-self assemble with the GRAS amphiphile gelators or coat the GRAS amphiphile gel to impart adhesion capability specific to cartilage or connective tissue. The cationic agents generally enhance the binding or adhesion of the gel to tissue or cells in vivo, thereby providing long residence time and concentrated accumulation of gel at a targeted site for controlled release of therapeutic agents. The cationic agent in the self-assembled gel enhances binding and adhesion to connective tissues (e.g., cartilage), principally through chondroitin 4-sulfate, chondroitin 6-sulfate, dermatan sulfate, hyaluronate, or other polysaccharides, as demonstrated by the specific reduction in such binding/adhesion following treatment of tissue with chondroitinase.

The cationic agents are generally included to form co-assembled or coated gel at a mass concentration that is smaller than that of the GRAS amphiphile gelators, but sufficiently high to impart adhesion capability to cartilage or connective tissue. For example, in the combined amount of GRAS amphiphile gelators and cationic agents, the cationic agent is in a concentration range greater than 5%, 6%, 7%, 8%, 9%, 10%, 11%, 12%, 13%, 14%, or 15% by weight, and no more than 40%, 45%, 50%, or 60% by weight. Preferably, the cationic agents are included at greater than 10% and no more than 50% in the combined amount of the cationic agents and the GRAS amphiphile gelators, e.g., any number in between the range such as 15%, 20%, 25%, or 30% (wt/wt). The amount of the cationic agents may depend on the adhesion properties, the mechanical property, and the drug loading of the resulting gel.

In some embodiments, suitable cationic agents are phospholipids, which co-assemble with the gelators through at least hydrophobic-hydrophilic interactions. In certain embodiments, the gelators and the cationic agents can both be integrated into the micro-/nano-structures of gel (e.g., lamellar, micellar, vesicular, or fibrous structures).

In other embodiments, suitable cationic agents are positively charged polysaccharides, which interact, non-covalently associate, or coat the self-assembled gel formed from GRAS amphiphile gelators.

Exemplary cationic polysaccharides to impart cartilage adhesion capability include chitosan, N-acyl chitosan, quaternized chitosan, alkyl chitosan, carboxy alkyl (aryl) chitosan, o-carboxyalkyl chitosan, N-carboxyacyl chitosan, thiolated chitosan, sugar derivatives of chitosan, cationic starch, cationic cellulose, cationic amylopectin, cationic galactan, cationic dextral, and their derivatives.

Exemplary cationic phospholipids to impart cartilage adhesion capability include 1,2-dioleoyl-3-trimethylammonium propane (DOTAP), 1,2-dioleyloxy-3-trimethylammonium propane chloride (DOTMA), or both.

Other examples of phospholipids bearing an overall positive charge are derivatives of ethylphosphatidylcholine, in particular di-esters of ethylphosphatidylcholine with fatty acids, such as 1,2-Distearoyl-sn-glycero-3-Ethylphosphocholine (Ethyl-DSPC or DSEPC), 1,2-Dipalmitoyl-sn-glycero-3-Ethylphosphocholine (Ethyl-DPPC or DPEPC). The negative counterion is preferably an halogen ion, in particular chlorine or bromine. Positively charged lipids include alkylammonium salts with a halogen counter ion (e.g. chlorine or bromine) comprising at least one ($C_{10}$-$C_{20}$) preferably ($C_{14}$-$C_{18}$), alkyl chain, such as, for instance mono or di-stearylammonium chloride, mono or di-hexadecylammonium chloride, dimethyldioctadecylammonium bromide (DDRB), hexadecyltrimethylammonium bromide (CrAB). Further examples of positively charged lipids are tertiary or quaternary ammonium salts with a halogen counter ion (e.g. chlorine or bromine) comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP).

In other forms, suitable cationic agents are amine-containing polymers. These cationic agents interact with the gelators and are at least inserted in the assembled micro-/nano-structure of gel.

Exemplary amine-containing polymers suitable for interaction with gelators and form co-assembled gel include polylysines and carboxymethyl chitosan. Generally the molecular weight of the amine-containing polymer is between about 100 and about 10,000, between about 300 and 2,500, or between about 500 and about 2,500.

The positively charged component is typically associated with a corresponding negative counter-ion, which can be mono- (e.g. halogen), di- (e.g. sulphate or methyl sulphate) or tri-valent (e.g. phosphate).

3. Therapeutic, Prophylactic and Diagnostic Active Agents

The gel compositions are suitable for delivery of one or more therapeutic, prophylactic or diagnostic agents to an individual or subject in need thereof, particularly at connective tissues concentrated with choindroitin or other polysaccharides such as cartilage. Therapeutic, prophylactic and diagnostic agents may be proteins, peptides, sugars or polysaccharides, lipids or lipoproteins or lipopolysaccharids, nucleic acids (DNA, RNA, siRNA, miRNA, tRNA, piRNA, etc.) or analogs thereof, or small molecules (typically 2,000 D or less, more typically 1,000 D or less, organic, inorganic, natural or synthetic) to repair or regenerate cartilage or treat disorders therewith.

In some forms, gelators may be prodrugs that hydrolytically or enzymatically degrade and release active agents.

In other forms, a therapeutic, prophylactic, or diagnostic agent may be physically entrapped, encapsulated, or non-covalently associated with the nanofibrous structures of the gel composition. The therapeutic, prophylactic, or diagnostic agents may be covalently modified with one or more gelators, one or more stabilizers, or be used as a gelator. Alternatively, they are incorporated into the assembled ordered lamellar, vesicular, and/or nanofibrous structures of the gel composition or positioned on the surface of the assembled structures.

Suitable actives include immunomodulatory agents including steroids, non-steroidal anti-inflammatories, chemotherapeutics, analgesics, anesthetics, joint lubricants such as glucosamine, chondroitin, and hyaluronic acid, antipyretic agents, anti-infectious agents such as antibacterial, antiviral and antifungal agents, tissue and/or bone regeneration promoters, vitamin, antioxidants, and small interfering RNA. The gels may also include a polymer such as poly (ethylene glycol) and poly(ethylene glycol)-di-acrylate, poly (ethylene oxide), carboxy methylcellulose, and poly(glycerol-co-sebasate acrylate), any derivative thereof, and/or a material such as chitosan any combination thereof.

In some embodiments, the self-assembled gel include genome editing nucleic acids that encode an element or elements that induce a single or a double strand break in the target cell's genome, and optionally a polynucleotide. An exemplary strand break inducing element is CRISPR/Cas-mediated genome editing composition. CRISPR is an acronym for Clustered Regularly Interspaced Short Palindromic Repeats; and they are often associated with genes which code for proteins that perform various functions related to CRISPRS, termed CRISPR-associated ("Cas") genes. A typical CRISPR/Cas system allows endogenous CRISPR spacers to recognize and silence exogenous genetic elements, either as a prokaryotic immune system or adopted as a genome editing tool in eukaryotes. (see, for example, Cong, Science, 15:339(6121):819-823 (2013) and Jinek, et al., Science, 337(6096):816-21 (2012)). By transfecting a cell with the required elements including a cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423.

In the context of an endogenous CRISPR system, formation of a CRISPR complex (including a guide sequence of CRISPR hybridized to a target sequence and complexed with one or more Cas proteins) results in cleavage of one or both strands in or near the target sequence. In the context of introducing exogenous CRISPR system into a target cell, one or more vectors may be included in the self-assembled gels to drive expression of one or more elements of a CRISPR system such that they form a CRISPR complex at one or more target sites in the target cell. The vectors may include one or more insertion sites (e.g., restriction endonuclease recognition sequence), a regulatory element operably linked to an enzyme-coding sequence encoding a CRISPR enzyme such as a Cas protein, or one or more nuclear localization sequences. Alternatively, a vector encodes a CRISPR enzyme that is mutated with respect to a corresponding wild-type enzyme such that the mutated CRISPR enzyme lacks the ability to cleave one or both strands of a target polynucleotide containing a target sequence.

Resources are available to help practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequence. For example, a practitioner interested in using CRISPR technology to target a DNA sequence (identified using one of the many available online tools) can insert a short DNA fragment containing the target sequence into a guide RNA expression plasmid. Detection of accumulation in the nucleus may be performed by any suitable technique, such as fusion to the CRISPR enzyme a detectable marker, immunohistochemistry to identify protein, or enzyme activity assay.

In some embodiments, when the self-assembled gel compositions include two or more agents, at least one agent potentiates efficacy of one or more remaining agents.

In some embodiments, the self-assembled gel compositions include a cocktail of factors for continuous delivery to promote migration of cells out of healthy tissue and into damaged cartilage area, thereby healing of injured cartilage. Exemplary factors include one or more of the following: bone morphogenetic protein (such as BMP-7), transforming growth factor beta, fibroflast growth factor, stromal cell-derived factor 1 (SDF1), protease inhibitors such as matrix metalloproteinase (MMP) inhibitor, Cathepsin-K inhibitor, and cystein proteinase inhibitor, and platelet rich plasma.

Exemplary Cathepsin-K inhibitors suitable for inclusion in the self-assembled gel composition include balicatib (AAE581), relacatib (SB-462795), odanacatibe (MK-0822), MV061194, MV061748, MV061940, MV061645, MSX-081, LL-006235, and bicyclic ketone.

Exemplary MMP inhibitors suitable for inclusion in the self-assembled gel composition include CL-82198, actinonin, PD166793, CP 471474, WAY 170523, and ageladine A.

In some embodiments, the self-assembled gel compositions further include pain management agents. Exemplary pain relief agents include local anesthetics such as lidocaine, procaine, tetracaine, dibucaine, or salts thereof.

In other embodiments, diagnostic agents are included in the self-assembled gel composition including paramagnetic molecules, fluorescent compounds, magnetic molecules, and radionuclides. Suitable diagnostic agents include, but are not limited to, x-ray imaging agents and contrast media. Radionuclides also can be used as imaging agents. Examples of other suitable contrast agents include gases or gas emitting compounds, which are radiopaque.

Cells

Cells are also suitable for inclusion in the viscous gel for delivery to connective tissue. These cells can be chondrocytes, progenitor or stem cells such as mesenchymal stem cells. Autologous chondrocytes are FDA approved. Mesenchymal stem cells (MSCs) are multipotent cells that are capable of differentiating into osteoblasts, chondrocytes, adipocytes, tenocytes, myoblasts, and neural cell lineages. (Pittenger M F, et al. *Science* 1999; 284:143-147). From a small, bone marrow aspirate obtained from adults, MSCs can be isolated, readily expanded due to their proliferative capacity, and characterized. (Friedenstein A, et al. *Cell Tissue Kinet* 1987; 20:263-72; Haynesworth S, et al. *J Cell Physiol* 1992; 138:8-16). Allogeneic MSCs in the self-assembled gel composition provide another approach for cartilage tissue regeneration.

The self-assembled gel may also be scaffolds for seeding of cells and implantation in vivo. The gel may be formulated with one or more bioactive molecules to enhance the survival, proliferation, and/or differentiation of seeded cells therein. The agents may be covalently bonded to the gelator or the cationic agents, or they may be non-covalently associated. An exemplary bioactive agent is polyamino acids (e.g., a peptide sequence containing arginylglycylaspartic acid, Arg-Gly-Asp) to improve cellular recognition and adhesion to the gel.

4. Solvents

The self-assembled gel composition can be prepared as a hydrogel or an organo-gel depending on the major solvent in the final formulation.

For most applications in vivo, a hydrogel is prepared. Some organic solvents, usually GRAS organic solvents or water-miscible organic solvents, may be used to facilitate dissolution and/or homogeneous mixture of gelators, cationic agents, and/or therapeutic agents, prior to addition of water or an aqueous salt solution. Following heating of the homogeneous mixture and subsequent cooling, a self-assembled gel composition is obtained. Further purification to remove organic solvents results in pharmaceutically acceptable hydrogel. Any residual amount of the organic solvent is generally within the stated limit of pharmaceutical products by the U.S. FDA, e.g., dicloromethane is below 600 ppm, methanol below 3,000 ppm, chloroform below 60 ppm, and within the limit by GMP or other quality based requirements.

In some forms, an organic solvent dissolves gelator, cationic agent, and optionally one or more therapeutic agents. An aqueous medium (e.g., saline) or water is added to the organic solution, followed by heating and optionally stirring, mixing, or vortexing to yield a homogeneous solution. After cooling to below the Krafft point of the gelator, e.g., to room temperature or body temperature, a viscous homogeneous gel forms, which is stable to inversion (e.g., would not flow when contained in an inverted vial).

In some embodiments, the organic solvent in the self-assembled gel is removed via dialysis, centrifugation, and/or filtration to yield suitable hydrogel formulation.

The organic solvent is selected based on the solubility of gelators therein, its polarity, hydrophobicity, water-miscibility, and in some cases the acidity. Suitable organic solvents include water-miscible solvent, or solvent that has an appreciable water solubility (e.g., greater than 5 g/100 g water), e.g., DMSO, dipropylene glycol, propylene glycol, hexyl butyrate, glycerol, acetone, dimethylformamide (DMF), tetrahydrofuran, dioxane, acetonitrile, alcohol such as ethanol, methanol or isopropyl alcohol, as well as low molecular weight polyethylene glycol (e.g., 1 kD PEG which melts at 37° C.). In other forms, the self-assembled gel compositions can include a polar or non-polar solvent, such as water, benzene, toluene, carbon tetrachloride, acetonitrile, glycerol, 1,4-dioxane, dimethyl sulfoxide, ethylene glycol, methanol, chloroform, hexane, acetone, N, N'-dimethyl formamide, ethanol, isopropyl alcohol, butyl alcohol, pentyl alcohol, tetrahydrofuran, xylene, mesitylene, and/or any combination thereof.

In other forms, the self-assembled gel compositions can include a polar or non-polar solvent, such as water, benzene, toluene, carbon tetrachloride, acetonitrile, glycerol, 1,4-dioxane, dimethyl sulfoxide, ethylene glycol, methanol, chloroform, hexane, acetone, N, N'-dimethyl formamide, ethanol, isopropyl alcohol, butyl alcohol, pentyl alcohol, tetrahydrofuran, xylene, mesitylene, and/or any combination thereof.

In other forms, an oil medium, for example, peanut oil, liquid paraffin or olive oil, is used.

Generally, the amount of an organic solvent is no more than 1:1, 1:2, 1:3, 1:4, 1:5, 1:6, 1:7, 1:8, 1:9, 1:10, or less in volume compared to the volume of an aqueous solution (e.g., water, aqueous buffer, aqueous salt solution, optionally containing a therapeutic agent). That is, the volume amount of an organic solvent in the total amount of liquid as used in forming a homogenous gel with high drug loading is generally less than about 50%, 33%, 25%, 20%, 17%, 14%, 12.5%, 11%, 10%, or 9%, and significantly less, typically less than 1%, for particles.

Gelators and organic solvents are selected at an appropriate gelator concentration and appropriate volume and ratio of the aqueous-organic mixture solvent system, or both, to form self-supporting gel. The gelator solution should not solidify or precipitate at 37° C. before the addition of an aqueous solution containing biologics or other therapeutic agent. Increasing the amount of the organic solvent or reducing the concentration of gelators in the organic solvent may prevent solidification of the gelator solution. When the gelator solution (in an organic solvent) is mixed with the aqueous solution containing biologics or other therapeutic agent, a self-supporting gel stable to inversion is formed, (following heating if necessary), rather than flowable mass/aggregates.

Following formation of self-supporting gels, the organic solvent in the gel may be removed to a residual level suitable for pharmaceutical applications. One or more purification techniques such as dialysis, centrifugation, filtration, drying, solvent exchange, or lyophilization, can be used. Residual organic solvent is within the stated limit of pharmaceutical products by the U.S. Food and Drug Administration (FDA) or below the acceptance criteria by U.S. Pharmacopeia Convention, International Conference on Harmonization guidance. For example, dicloromethane is below 600 ppm, methanol below 3,000 ppm, chloroform below 60 ppm; and within the limit by GMP or other quality based requirements.

5. Properties

Hydrogels offer advantages such as the ability to hydrate in aqueous conditions and enhanced biological compatibility, and can be well suited for biological administration (e.g., implantation of wet hydrogels). The self-assembled gels can increase stability of agents, such as encapsulated therapeutic agents and/or vitamins, e.g., from photo/ultra-violet degradation, and can deliver high concentrations of vitamins or GRAS agents.

Surface Charge & Adhesion

Some embodiments provide the self-assembled gel composition possess a $\zeta$-potential of between about 50 mV and about $-20$ mV, between about 30 mV and about $-10$ mV, or are positively charged overall. The positively charged gel composition may electrostatically interact or physically entangle with the proteoglycan or other biomolecules in the connective tissue.

The self-assembled gel composition containing the cationic agent adheres significantly more to cartilage compositions or a connective tissue than self-assembled gel composition lacking the cationic agent.

Mechanical Property & Injectability

In some embodiments, the self-assembled gel compositions are lubricious and/or have recoverable rheological properties. In some embodiments, the self-assembled gel compositions have an elastic modulus of from 10 to 10,000 Pascal and a viscous modulus of from 10 to 10,000 Pascal.

With self-assembled gel compositions, no gravitational flow is observed upon inversion of a container at room temperature for at least 10 seconds, and in some cases, for about 1 hour, 3 hours, 1 day, 2 days, or longer. A self-assembled gel is homogeneous and stable to inversion, unlike heterogeneous materials that is a mixture of gelled regions (non-flowable) and non-gelled, liquid regions (flowable). A self-assembled gel is also different from liposome or micelle suspensions. Liposome or micelles suspensions are not self-supporting and can flow when the container is inverted.

In preferred embodiments, the self-assembled gel compositions are injectable or implantable adhesive hydrogel, suitable for cartilage healing and repair. Due to the non-covalent interactions for the assembly of gelators and cationic agents, a bulk gel may deform and be extruded under a shear force (e.g., during injection), and the gelators and cationic agents re-assemble upon cessation of shear forces to a self-supporting, stable-to-inversion state (e.g., elastic modulus G' greater than viscous modulus G"). Alternatively, the self-assembled gel composition may be processed into microparticles or nanoparticles and be suspended in a pharmaceutically acceptable carrier, which is injectable as a suspension, or applied as a dry powder containing nanostructures alone or in the gel.

Micro- and/or Nano-Structures

The agents can be encapsulated within or between the nanostructures, can be non-covalently bonded to the nanostructures, or both.

When amphiphilic molecules self-assemble in a solvent, the hydrophobic and the hydrophilic portions of the gelator molecules can interact to form lamellae of gelator molecules. In some embodiments, when the gels are hydrogels, the hydrophobic portions of gelators are located in the inner regions of a given lamella, and hydrophilic portions are located at the outer surfaces of the lamella. In some embodiments, when the gels are organogels, the hydrophobic portions of gelators are located in the outer regions of a given lamella, and hydrophilic portions are located at the inner surfaces of the lamella. The lamella can have a width of from about three (e.g., from about four) to about five (e.g., to about four) nanometers and a length of several microns (e.g., one micron, two microns, three microns, four microns, five microns, ten microns, twenty microns, or twenty five microns) or more. Several tens or hundreds of such lamellae can bundle together to form nanostructures, such as fibers and sheet-like structures. In some embodiments, the nanostructures can include nanoparticles, micelles, liposome vesicles, fibers, and/or sheets.

In some embodiments, the nanostructures can have a minimum dimension (e.g., a thickness, a width, or a diameter) of 2 nm or more (e.g., 50 nm or more, 100 nm or more, 150 nm or more, 200 nm or more, 250 nm or more, 300 nm or more, 350 nm or more) and/or 400 nm or less (e.g., 350 nm or less, 300 nm or less, 250 nm or less, 200 nm or less, 150 nm or less, 100 nm or less, or 500 nm or less). In some embodiments, the nanostructures (e.g., fibers, sheets) can have a length and/or width of several microns (e.g., one micron, two microns, three microns, four microns, five microns, ten microns, twenty microns, or twenty five microns) or more. The nanostructures can aggregate into networks, and/or be in the form of a liquid crystal, emulsion, fibrillar structure, or tape-like morphologies. When the nanostructures are in the form of fibers, the fibers can have a diameter of about 2 nm or more, and can have lengths of hundreds of nanometers or more. In some embodiments, the fibers can have lengths of several microns (e.g., one micron, two microns, three microns, four microns, five microns, ten microns, twenty microns, or twenty five microns) or more.

Degradation

In some embodiments, the gel compositions disassemble preferentially under conditions present in a disease state of a cell, tissue or organ, thus allowing for release of an agent at targeted tissue and/or organ.

In one aspect, the disclosure features self-assembled gel compositions capable of controlled release of agents. The self-assembled gel compositions include enzyme-cleavable, generally recognized as safe (GRAS) first gelators having a molecular weight of 2500 or less; and one or more agents.

For example, the gel compositions can include degradable linkages that are cleavable upon contact with an enzyme and/or through hydrolysis, such as ester, amide, anhydride, a thioester, and carbamate linkages. Typically, linkage is always between hydrophilic and hydrophobic parts of the amphiphile molecule. In some embodiments, phosphate-based linkages can be cleaved by phosphatases. In some embodiments, labile linkages are redox cleavable and are cleaved upon reduction or oxidation (e.g., —S—S—). In some embodiments, degradable linkages are susceptible to temperature, for example cleavable at high temperature, e.g., cleavable in the temperature range of 37-100° C., 40-100° C., 45-100° C., 50-100° C., 60-100° C., 70-100° C. In some embodiments, degradable linkages can be cleaved at physiological temperatures (e.g., from 36 to 40° C., about 36° C., about 37° C., about 38° C., about 39° C., about 40° C.). For example, linkages can be cleaved by an increase in temperature. This can allow use of lower dosages, because agents are only released at the required site. Another benefit is lowering of toxicity to other organs and tissues. In certain embodiments, stimuli can be ultrasound, temperature, pH, metal ions, light, electrical stimuli, electromagnetic stimuli, and combinations thereof.

Degradation (Cleavable Linkage)

Stimuli evoking release can be present due to the characteristics at the site of administration or where release is desired, for example, tumors or areas of infection. These may be conditions present in the blood or serum, or conditions present inside or outside the cells, tissue or organ. These are characterized by low pH and the presence of degradative enzymes. The gel compositions may be designed to disassemble only under conditions present in a disease state of a cell, tissue or organ, e.g., inflammation, thus allowing for release of an agent at targeted tissue and/or organ. This is an alternative or may be used in combination to gel erosion-mediated and passive diffusion-mediated release of agent.

This responsive release is based on linkages formed from degradable chemical bonds (or functional groups) and/or tunable non-covalent association forces (e.g., electrostatic forces, van der Waals, or hydrogen bonding forces). In some embodiments, these linkages are (1) degradable covalent linkage between the hydrophilic segment and the hydrophobic segment of an amphiphile gelator, (2) positioned in a prodrug-type gelator, which upon cleavage releases an active drug, and/or (3) covalent linkage or non-covalent association forces between a gelator and a therapeutic agent. The cleavage or dissociation of these linkages result in (1) more rapid or greater release of the encapsulated or entrapped agents compared to passive diffusion-mediated release of agent; and/or (2) converts prodrug gelator into active drug for release.

Stimuli evoking release includes intrinsic environment in vivo and user-applied stimulation, for example, enzymes, pH, oxidation, temperature, irradiation, ultrasound, metal ions, electrical stimuli, or electromagnetic stimuli. A typical responsive linkage is cleavable through enzyme and/or hydrolysis, based on a chemical bond involving an ester, an amide, an anhydride, a thioester, and/or a carbamate. In some embodiments, phosphate-based linkages can be cleaved by phosphatases or esterase. In some embodiments, labile linkages are redox cleavable and are cleaved upon reduction or oxidation (e.g., —S—S—). In some embodiments, degradable linkages are susceptible to temperature, for example cleavable at high temperature, e.g., cleavable in the temperature range of 37-100° C., 40-100° C., 45-100° C., 50-100° C., 60-100° C., 70-100° C. In some embodiments, degradable linkages can be cleaved at physiological temperatures (e.g., from 36 to 40° C., about 36° C., about 37° C., about 38° C., about 39° C., about 40° C.). For example, linkages can be cleaved by an increase in temperature. This can allow use of lower dosages, because agents are only released at the required site. Another benefit is lowering of toxicity to other organs and tissues. In certain embodiments, stimuli can be ultrasound, temperature, pH, metal ions, light, electrical stimuli, electromagnetic stimuli, and combinations thereof.

The gel compositions can be designed for controlled degradation at a site or after a period of time, based on the conditions at the site of administration. Compared to free agent in a solution, the encapsulated agent releases from the self-assembled gel much slower, for example, less than 30% of encapsulated agent is released in the first three days and less than 70% in seven days. In the presence of a stimulus such as an enzyme, self-assembled gel formed from a gelator with an enzyme-degradable linkage releases the agent more rapidly, compared to the gel in a medium lacking the enzyme.

In other embodiments, the self-assembled gel serves as a scaffold that adheres and remain in connective tissue sites for at least 3 days, 5 days, 1 week, 2 weeks, 3 weeks, 1 month, 2 months, 3 months, or longer, for the healing of injured cartilage by allowing endogenous or exogenous cells to grow and proliferate in there. The degradation can commensurate with the growth of new tissue, e.g., cartilage. The self-assembled gel composition degrades at a rate to substantially maintain structural support during the initial stages of formation, but also allows space for continuous growth of new cartilage tissue.

Release

When applied to a biological system, the self-assembled gel compositions can provide controlled release of agents. The gel compositions can be adapted to be controllably disassembled.

Stimuli evoking release can be present due to the characteristics at the site of administration or where release is desired.

In some embodiments, the self-assembled gel composition release therapeutic agents in connective tissue following administration over at least 3 days, 5 days, 1 week, 2 weeks, 3 weeks, 1 month, 2 months, 3 months, or longer.

6. Formulation

The self-assembled gel composition with affinity to connective tissues may be prepared in dry powder formulations or liquid formulations.

Generally the formulation is sterilized or sterile. For example, a sterile formulation can be prepared by first performing sterile filtration of gelators, cationic agents, as well as agents to be encapsulated, followed by processes of making in an aseptic environment. Alternatively, all processing steps can be performed under non-sterile conditions, and then terminal sterilization (e.g., gamma or E-beam irradiation) can be applied to the formed particles or lyophilized product.

Dry formulations contain lyophilized self-assembled gel compositions where solvent is removed, resulting in xerogels. Xerogels can be in a powder form, which can be useful for maintaining sterility and activity of agents during storage and for processing into desired forms. As xerogels are solvent free, they can have improved shelf-life and can be relatively easily transported and stored. To lyophilize self-assembled gels, the gels can be frozen (e.g., at −80° C.) and vacuum-dried over a period of time to provide xerogels.

Alternatively, a dry formulation contains dry powder components of gelators, cationic agents, one or more therapeutic agents, which are stored in separate containers, or mixed at specific ratios and stored. In some embodiments, suitable aqueous and organic solvents are included in additional containers. In some embodiments, dry powder components, one or more solvents, and instructions on procedures to mix and prepare assembled nanostructures are included in a kit.

Liquid formulations contain self-assembled gel composition suspended in a liquid pharmaceutical carrier. In some forms, self-assembled gel is suspended or resuspended in aqueous media for ease of administration and/or reaching a desired concentration for minimizing toxicity.

Suitable liquid carriers include, but are not limited to, distilled water, de-ionized water, pure or ultrapure water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human. The liquid formulations may be isotonic relative to body fluids and of approximately the same pH, ranging from about pH 4.0 to about pH 8.0, more preferably from about pH 6.0 to pH 7.6. The liquid pharmaceutical carrier can include one or more physiologically compatible buffers, such as a phosphate or bicarbonate buffers. One skilled in the art can readily determine a suitable saline content and pH for an aqueous solution that is suitable for an intended route of administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

III. Methods of Making

Generally, a process to make the self-assembled gel composition includes combining gelators, cationic agents, therapeutic agents, and solvents to form a mixture; heating or sonicating the mixture; stirring or shaking the mixture for a time sufficient to form a homogeneous solution; and cooling the homogenous solution for a time sufficient to enable the formation of self-assembled gel compositions.

An organic solvent (e.g., DMSO, methanol, isopropanol) may be used to dissolve and mix gelators, cationic agent and/or drug agents depending on their solubility in the organic phase. Water or an aqueous salt solution is added to introduce the water component. The mixture can be heated and/or sonicated and/or placed in a bath to completely dissolve the gelator, drug and any other solid ingredients to form a homogeneous solution, and the solution is then cooled under controlled conditions (e.g., temperature controlled vessel or water bath) and/or rested in an undisturbed location. The solution can transition into a viscous gel after a given time period. Gelation is deemed complete when no gravitational flow is observed upon inversion of the container at room temperature for at least 10 seconds, and in some cases, for about 1 day, 3 days, 1 week, 2 weeks, or longer. A self-assembled gel is homogeneous and stable to inversion, unlike heterogeneous materials that is a mix of gelled regions (non-flowable) and non-gelled, liquid regions (flowable).

The organic solvent in the self-assembled hydrogel can be substantially removed via vacuum, lyophilization, centrifugation, washing, dialysis etc., in one or more repeated processes to reduce residual amounts of organic solvents to below the stated limit of pharmaceutical product requirements.

Sterile injectable solutions can be prepared. For example a sterile formulation can be prepared by first performing sterile filtration of the process solutions (e.g., drug and gelator solutions), followed by gel preparation, suspension, purification and lyophilization under aseptic procession conditions. Alternatively, all processing steps can be performed under non-sterile conditions, and then terminal sterilization (e.g., gamma or E-beam irradiation) can be applied to the lyophilized hydrogel product. Sterile solution for resuspension can also be prepared using similar methods.

In some embodiments, the self-assembled gel is further processed into particles for ease of administration or other purposes. The gel compositions may be suspended in an aqueous solution, homogenized, isolated, or combined. In some forms, the bulk gel is suspended in water and/or phosphate buffered saline with physiological salt concentrations, and homogenized or sonicated to break up the bulk gel into particles which retain the fibrous nanostructures formed in the bulk gel.

IV. Methods of Using

The self-assembled gel composition may be used as lubrication to prevent and/or repair cartilage damage.

The self-assembled gel composition may provide a biocompatible scaffold for cartilage cells to growth and proliferate, thus promoting healing of damaged cartilage.

The self-assembled gel composition may bind, adhere, or preferentially accumulate at a connective tissue for controlled release of therapeutic agents. Connective tissue includes cartilage, tendons, ligaments and other avascular tissues in the body, as well as precursors thereof such as chondrocytes. It is understood that the composition may be applied not just to cartilage and other differentiated avascular tissue, but tissue which will differentiate or mature into connective tissue. The formulations may also be applied to other tissues to which the formulation similarly adheres due to the inclusion of the cationic compound.

The self-assembled gel composition may deliver chondrocyte in an autologous chondrocyte implantation procedure; delivery and differentiate stem cells for cartilage regeneration; or both, optionally concurrently with delivery of a cocktail of actives.

In generally, injectable, adhesive gel composition to cartilage may be supplement or replace surgical procedures for cartilage repair by improving therapeutic efficacy and reducing complications or negative sequelae associated with surgical procedure.

In some forms, the self-assembled gel composition is used to treat and/or repair cartilage tissue in a subject by administering to a subject an effective amount of the self-assembled gel composition in a pharmaceutically acceptable form, wherein the self-assembled gel composition is effective for supporting, promoting, and/or enhancing the growth, regeneration, and/or repair of cartilage.

In some forms, the self-assembled gel composition is used in a method of treating and/or repairing cartilage tissue in a subject by administering to a subject an effective amount of the self-assembled gel composition, wherein chondrocytes, progenitor or stem cells are seeded onto the self-assembled gel composition either prior or subsequent to administration.

In some forms, a method of treating arthritis is provided by administering to a subject an effective amount of the self-assembled gel composition effective for alleviating or ameliorating the symptoms of arthritis in the subject.

The present invention will be further understood by reference to the following non-limiting examples.

EXAMPLES

Example 1: Ascorbyl Palmitate (AP) and 1,2-dioleoyl-3-trimethylammonium propane (DOTAP) Co-Self Assembled into Nanostructured Gel with Enhanced Adhesion to Cartilage and Responsive-Release of Encapsulated Agents Materials and Methods A GRAS amphiphile (80 mg), here ascorbyl palmitate in this Example, and DOTAP (20 mg) were weighed into a scintillation vial. DOTAP refers to N-[1-(2,3-Dioleoyloxy) propyl]-N,N,N-trimethylammonium methyl-sulfate. The mixture in the presence of 1 mL water-DMSO (4:1 volume ratio) was heated until it dissolved. The solution was allowed to cool down to room temperature on a flat and stable surface. Gelation was complete when no gravitational flow was observed upon inversion of the vial. Gelation could take between 15 and 45 minutes.

To prepare gels for adhesion experiments, a fluorescent dye, lipophilic carbocyanine DiOC18(7) ("DiR") was encapsulated within the gel. Specifically, 40 µl DiR solution (2.5 mg/ml) in DMSO was added during the gel preparation process.

For adhesion assay of DiR-loaded hydrogel to cartilage, 50 µL hydrogel was applied to bovine cartilage explant (6 mm in diameter) and incubated at 37° C. for 1 hour. After 1 h, cartilage explants were washed twice with PBS and imaged using in vivo imaging system (IVIS) Hydrogels both with and without DOTAP were evaluated. Hydrogels without DOTAP were prepared using similar method as described above without using DOTAP, and 100 mg GRAS amphiphile was used. Untreated cartilage (blank control) and cartilage treated with free dye were used as control.

Results

Gels were prepared from the co-assembly between ascorbyl palmitate and DOTAP; denoted as AP-DOTAP gel. The gel morphology was characterized using scanning electron microscopy (SEM) and was found to be nanofibrous. Gels showed a high positive surface charge with zeta potential values of over +45 mV.

FIG. 1 shows the positively charged gels (AP-DOTAP gels) preferentially and rapidly adhered to the cartilage explants, which showed potential for delivering encapsulated agents specifically to cartilage upon their intra-articular administration. AP-DOTAP gels showed higher adhesion to cartilage than AP-only gels, which indicated improved specificity for cartilage due to the addition and co-assembly with DOTAP. Pretreatment of cartilage with chondroitinase ABC for 24 hours to reduce the percentage of glycosaminoglycans (GAG) resulted in a decrease in adhesion of AP-DOTAP gels, indicating that specificity of AP-DOTAP gel for cartilage was mediated through its interaction with GAG in cartilage.

Figure 2:
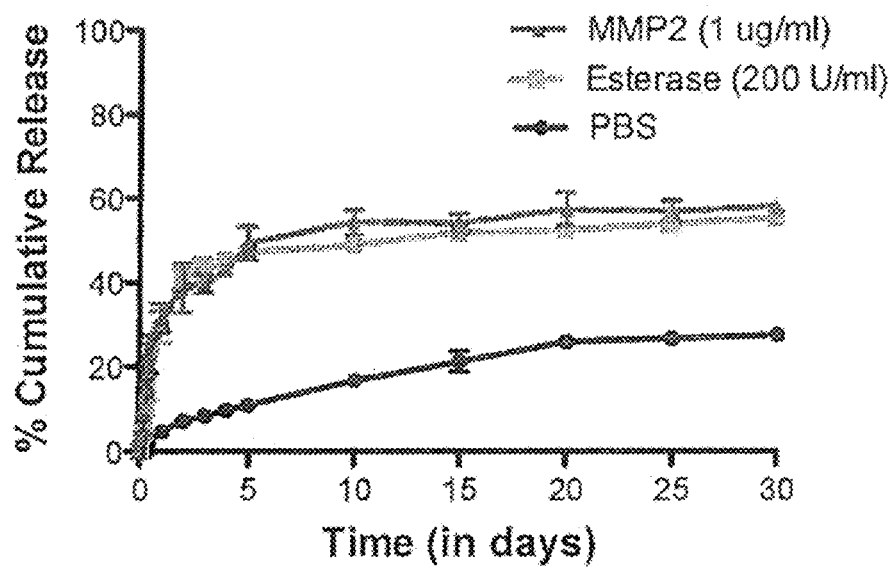
FIG. 2 is a line graph showing the cumulative release (%) of CL-82198 (an inhibitor to matrix metallopeptidase 13, MMP-13) over time (days) from AP-DOTAP co-assembled gels in phosphate buffered saline (PBS) (line connecting circles), in PBS with MMP-2 at 1 µg/mL (line connecting triangles), or in PBS with esterase at 200 U/mL (line connecting squares).
Figure 3:
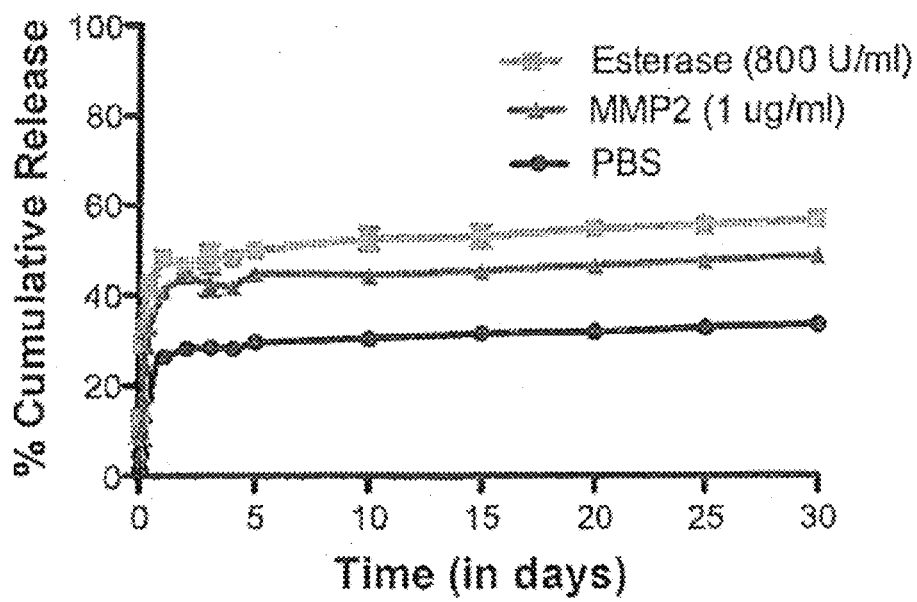
FIG. 3 is a line graph showing the cumulative release (%) of L-006235 (a Cathepsin-k inhibitor) over time (days) from AP-DOTAP co-assembled gels in phosphate buffered saline (PBS) (line connecting circles), in PBS with MMP-2 at 1 µg/mL (line connecting triangles), or in PBS with esterase at 800 U/mL (line connecting squares).

FIGS. 2 and 3 show AP-DOTAP gel stably encapsulated CL-82198 (an MMP-13 inhibitor) and LL-006235 (a Cathepsin-k inhibitor), respectively, under a normal physiological-like condition (in phosphate buffered saline, PBS) for at least 30 days. This positively charged AP-DOTAP hydrogel showed release of encapsulated therapeutics in response to enzymes, including esterase and MMPs, which are up-regulated during joint inflammation (FIGS. 2 and 3).

Figure 4:
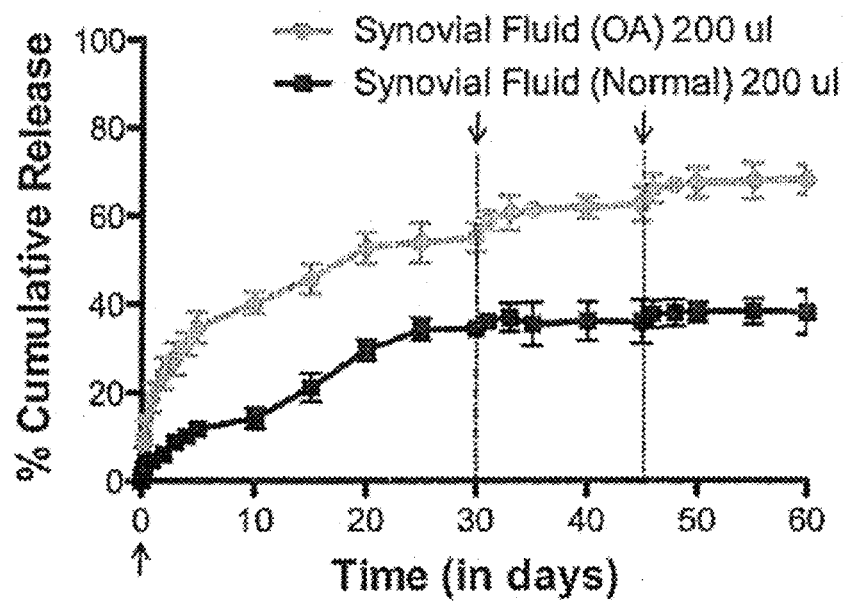
FIG. 4 is a line graph showing the cumulative release (%) of CL-82198 over time (days) from AP-DOTAP co-assembled gels in the presence of synovial fluid from osteoarthritis (OA) patients (line connecting circles), or in the presence of synovial fluid from normal human subjects (line connecting squares).
Figure 5:
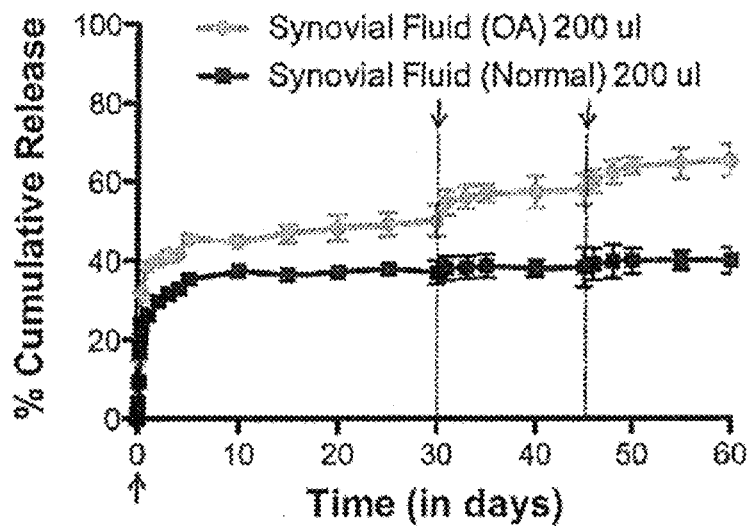
FIG. 5 is a line graph showing the cumulative release (%) of L-006235 over time (days) from AP-DOTAP co-assembled gels in the presence of synovial fluid from osteoarthritis (OA) patients (line connecting circles), or in the presence of synovial fluid from normal human subjects (line connecting squares).

FIGS. 4 and 5 show AP-DOTAP gel had significantly higher release of encapsulated CL-82198 and L-006235, respectively, in response to synovial fluid from osteoarthritis (OA) patients in comparison to the release in response to the synovial fluid from normal humans (Normal).

Figure 6:
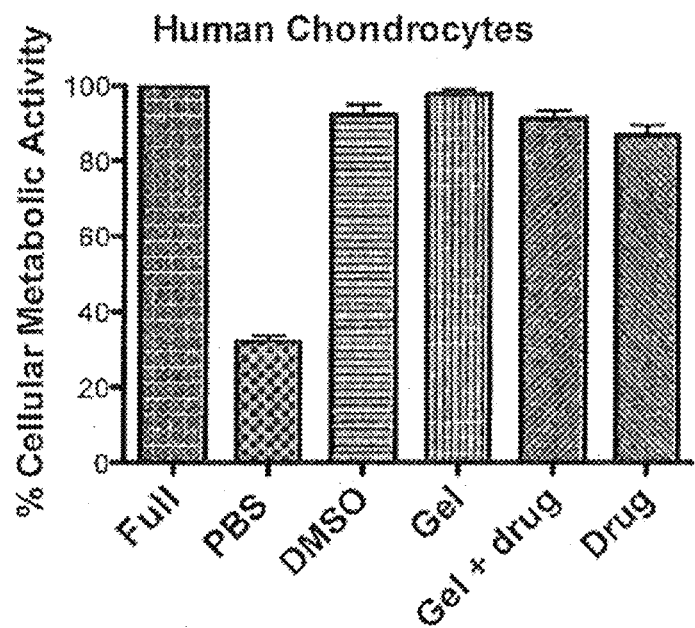
FIG. 6 is a bar graph showing the percentage of cellular metabolic activity of cultured chondrocytes, derived from normal human knee, in PBS, in dimethyl sulfoxide (DMSO), in AP-DOTAP co-assembled gel (Gel), in AP-DOTAP co-assembled gel loaded with CL-82198 (Gel+drug), or in the presence of CL-82198 (Drug).
Figure 7:
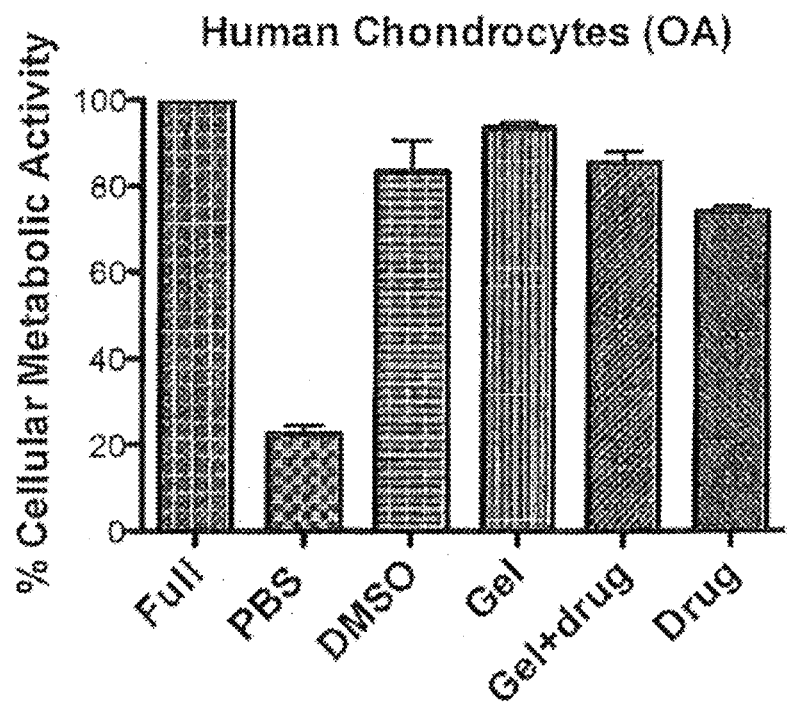
FIG. 7 is a bar graph showing the percentage of cellular metabolic activity of cultured chondrocytes, derived from osteoarthritic-positive human knee, in PBS, in dimethyl sulfoxide (DMSO), in AP-DOTAP co-assembled gel (Gel), in AP-DOTAP co-assembled gel loaded with CL-82198 (Gel+drug), or in the presence of CL-82198 (Drug).

FIGS. 6 and 7 show AP-DOTAP gel was cytocompatible with chondrocytes from a normal donor and with chondrocytes from an OA positive donor, respectively, which was believed to show that intraarticular administration of the gel would not result in a detrimental effect to either healthy or diseased cartilage. These tested chondrocytes were derived from cartilage from the knees of respective human subjects.

Example 2: AP-DOTAP Co-Assembled Gel Loaded with a Cathepsin-k Inhibitor Prevented Cartilage Degeneration in a Rat Osteoarthritis Model Methods The therapeutic efficacy of L-006235-loaded AP-DOTAP hydrogel was evaluated in a medial meniscal tear model of osteoarthritis developed in Lewis rats. Medial meniscal tear surgery was performed in the right knee of all the rats on day 0. Seven days following surgery, rats were randomized into two groups, i.e., group 1: treated with Cat-K inhibitor (L-006235) loaded hydrogel, and group 2: untreated disease control. Two doses, one on day 7 and one on day 14, of AP-DOTAP gel (10% w/w) loaded with a Cat-K inhibitor (L-006235) at 10 mg/mL were injected intraarticularly. Animals were sacrificed on day 21 for histological analysis.

Results

Figure 8:
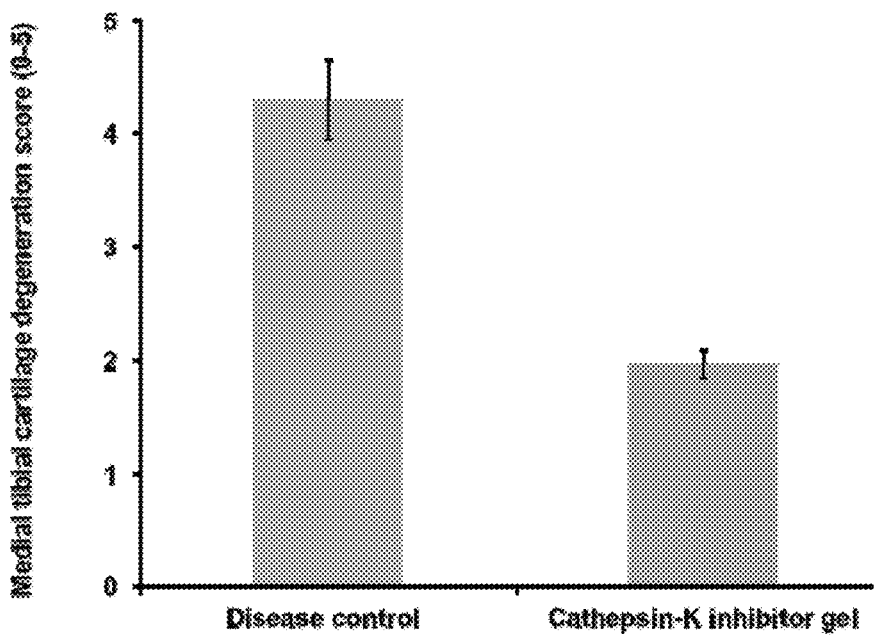
FIG. 8 is a bar graph comparing the scores of medial tibial cartilage degeneration of rats without and those with AP-DOTAP co-assembled gel (10% w/w) loaded with 10 mg/mL Cathepsin-K inhibitor (L-006235).

FIG. 8 shows rats administered with AP-DOTAP gel delivering Cathepsin-k inhibitor had a much lower degeneration on day 21 following medial meniscal tear, compared to rats in the disease control group.

Example 3: Gels Co-Assembled Between Other GRAS Amphiphiles (Than Ascorbyl Palmitate) and DOTAP Enhanced Adhesion to Cartilage Compared to GRAS Amphiphile-Alone Gels Materials and Methods GRAS amphiphiles in this Example included triglycerol monostearate (TG18), sucrose palmitate (SP), and sucrose stearate (SS). These amphiphiles were individually co-assembled with DOTAP, forming TG18-DOTAP gel, SP-DOTAP gel, and SS-DOTAP gel, respectively. The amounts of each component were as described in Example 1. Therefore, 80 mg amphiphile gelator and 20 mg DOTAP, thus 20% (w/w) DOTAP in the combined amount of solid component; forming a gel in a 1 mL liquid medium, therefore 100 mg solid mass in 1 mL liquid medium resulting in 10 w/v % gels.

For an adhesion assay, 10% (w/v) gels loaded with a fluorescent dye (DiR) were prepared. 50 µl gel was applied to each explant of bovine cartilage (6 mm in diameter) and incubated at 37° C. for 1 hour. After 1 hour, cartilage explants were washed with PBS and imaged using in vivo imaging system (IVIS) (n=3). Hydrogels without DOTAP were prepared where 100 mg of the GRAS amphiphile was used, without using DOTAP. Untreated cartilage (blank control) and cartilage treated with free dye were used as control.

Results

Figure 9:
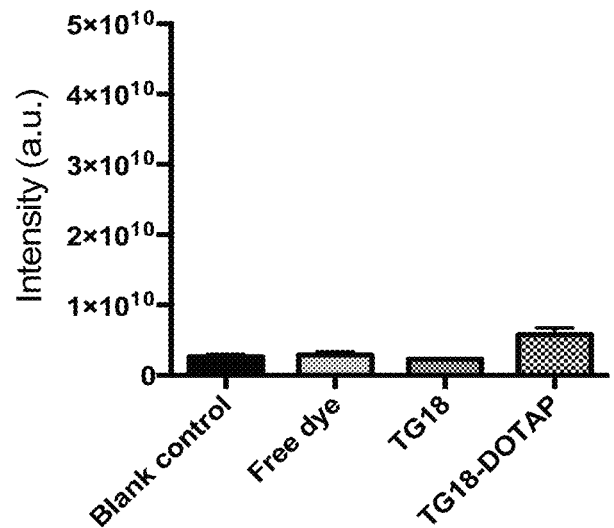
FIGS. 9-11 are bar graph showing the fluorescence intensity (arbitrary unit, A.U.) of cartilage explants following a 1-hour incubation with specimens loaded with or being a fluorescent dye.

FIG. 9 shows co-self assembly of DOTAP with triglycerol monostearate (TG18) resulted in a significant increase in adhesion to cartilage, compared to TG18-alone gel.

Figure 10:
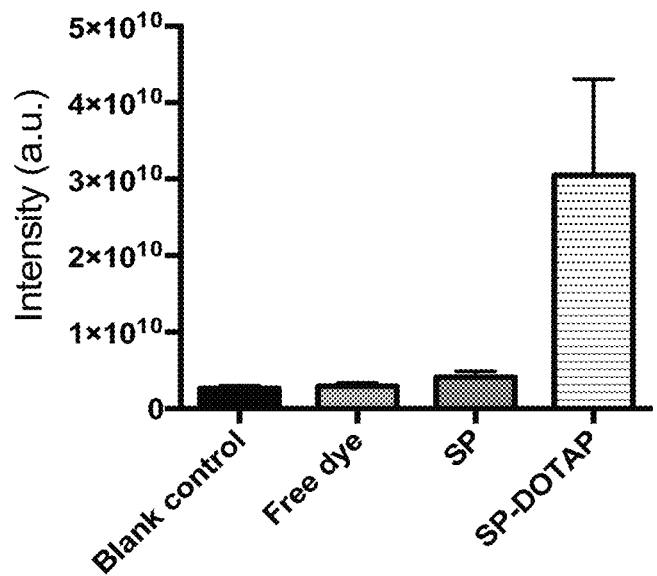

FIG. 10 shows co-self assembly of DOTAP with sucrose palmitate (SP) resulted in a remarkable increase in adhesion to cartilage, compared to SP-alone gel.

Figure 11:
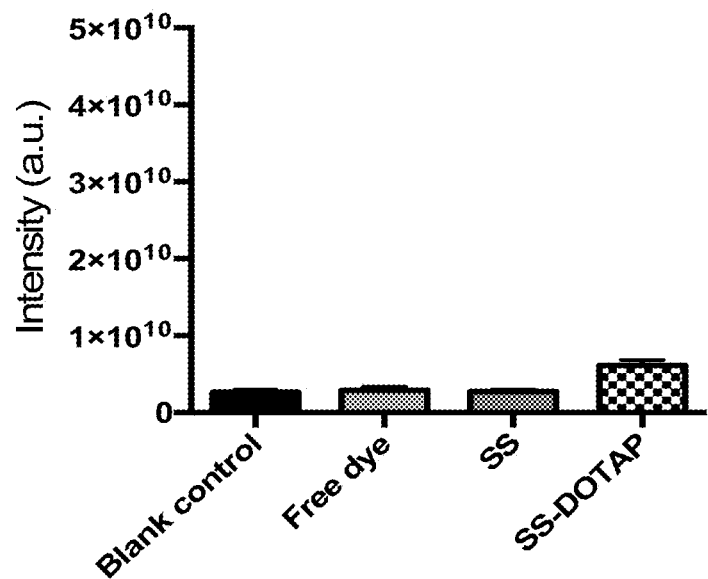

FIG. 11 shows co-self assembly of DOTAP with sucrose stearate (SS) resulted in a significant increase in adhesion to cartilage.

Table 1 summaries data in Example 1 and this Example that SP-DOTAP gel showed maximal cartilage adhesion among four types of gels: i.e., AP-DOTAP, TG18-DOTAP, SS-DOTAP, and SP-DOTAP. Higher adhesion seen with SP-DOTAP may be due to more hydrophilicity of SP compared to other GRAS amphiphiles.

TABLE 1

Comparison of hydrophilicity of GRAS amphiphiles and mean radiant intensity from the cartilage surface after incubation with co-self assembled gels between a GRAS amphiphile and DOTAP.

| GRAS amphiphile | Log P | Mean radiant intensity from the cartilage surface ($\times 10^{10}$) |
|---|---|---|
| SP | 0.64 | 3.05 |
| SS | 1.416 | 0.61 |
| TG18 | 3.899 | 0.57 |
| AP | 4.62 | 0.39 |

(log P is the partition coefficient of a molecule between an aqueous and lipophilic phases, usually octanol and water; commonly used as a measure of lipophilicity of a compound.)

Example 4: Incorporation of DOTAP Did not Affect the Stability of the Encapsulated Drug in a Self-Assembled Hydrogel Methods SP-DOTAP gel was assayed for its ability to retain the encapsulated Cathepsin-K inhibitor, L-006235, loaded at 10% (w/w). In vitro release of L-006235 from SP-only hydrogel and from SP-DOTAP hydrogel was evaluated in PBS at 37° C. Drug-loaded hydrogels (200 µL, 10 mg drug/mL) further suspended in PBS (800 µl) were placed in dialysis tubing (8-10 kD molecular weight cut-off, Spectrum Labs). The dialysis bags filled with hydrogel in the suspension medium were placed in a 40 mL sink medium (PBS), and incubated at 37° C. with a shaking speed of 150 rpm. At each time point, an aliquot (1 ml) from the sink medium was removed and replenished with the same volume of fresh PBS to ensure constant sink conditions. Aliquots were lyophilized and dissolved in 250 µL methanol, followed by high performance liquid chromatography (HPLC) analysis of the drug amount.

Results

An in vitro release study in PBS at 37° C. showed less than 10% cumulative release of the Cathepsin-K inhibitor (L-006235) in 7 days. L-006235 is a disease modifying osteoarthritis drug (DMOAD).

Figure 12:
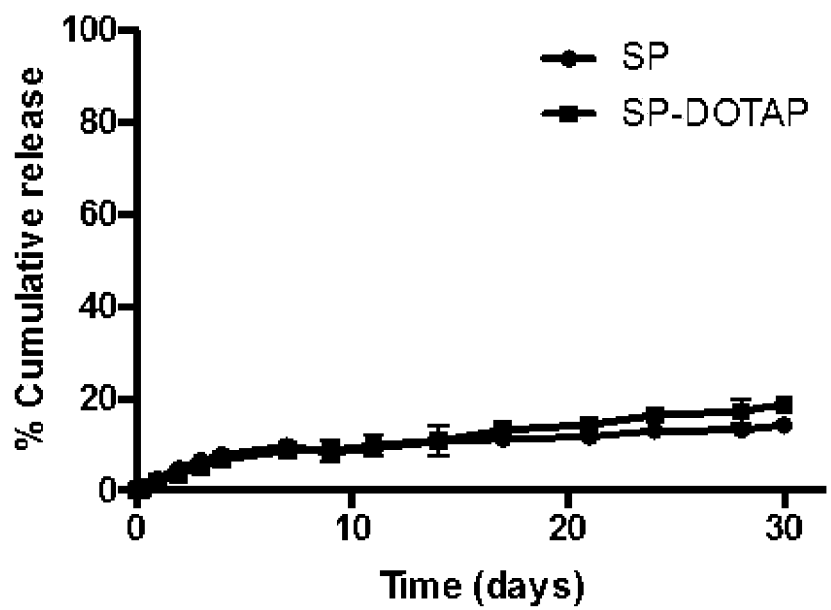
FIG. 12 is a line graph showing the cumulative release (%) of encapsulated L-006235 over time (days) from sucrose palmitate hydrogel (SP, data points shown as circles) or from hydrogel from the co-assembly between sucrose palmitate and DOTAP (SP-DOTAP, data points shown in squares).

FIG. 12 shows in a 30-day study, both SP and SP-DOTAP gels showed less than 20% cumulative release of L-006235, with similar release kinetics, which was indicative that incorporation of DOTAP into hydrogel did not affect the stability of the encapsulated drug.

Example 5: Effect of the Relative Amount of DOTAP to Amphiphile Gelator on Cartilage Adhesion Capability of DOTAP-Sucrose Palmitate Co-Self Assembled Gel, as Well as Penetration into Cartilage Methods DiR loaded SP-DOTAP hydrogels were prepared as described in Example 3 with varying concentrations of DOTAP. Specifically, the DOTAP concentration in the gelator mixture (i.e., the combination of DOTAP and SP) was varied between 5-20% (w/w). DiR-loaded SP hydrogel prepared using 100 mg of SP were used as control. Untreated cartilage (blank control) and cartilage treated with free dye were also used as control. Adhesion was tested using a method as described in Examples 1 and 3.

To determine the penetration of gels into the cartilage, SP-DOTAP gels where DOTAP was included at 15% (w/w) of the gelator mixture (i.e., the combination of DOTAP and SP) was assayed. 504 SP-only hydrogel or SP-DOTAP hydrogel was applied to bovine cartilage explant (6 mm in diameter) and incubated at 37° C. for 24 hour. After 24 h, cartilage explants were washed twice with PBS and the surface of the cartilage was scraped off using a brush to remove surface adhered hydrogel. Cartilage explants were imaged using in vivo imaging system (IVIS). Untreated cartilage (blank control) and cartilage treated with free dye were used as control.

Results

Figure 13:
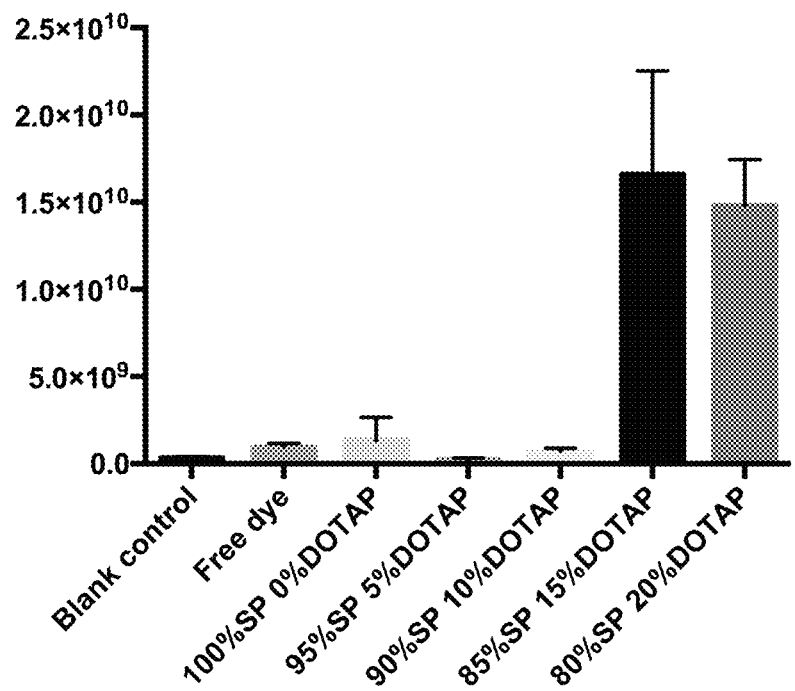
FIG. 13 is a bar graph showing the fluorescence intensity (arbitrary unit, A.U.) of cartilage explants following a 1-hour incubation with different compositions of gels loaded with a fluorescent dye. The gels were formed from the spontaneous assembly following heating and cooling of (1) sucrose palmitate (SP) alone, without the addition of DOTAP; (2) 95% SP and 5% DOTAP (weight percentage); (3) 90% SP and 10% DOTAP; (4) 85% SP and 15% DOTAP; (5) 80% SP and 20% DOTAP.

FIG. 13 shows greater than 10% (w/w) DOTAP in the gelator mixture, i.e., a mass ratio of DOTAP to sucrose palmitate that is greater than 1:9, was required to achieve cartilage adhesion.

Figure 14:
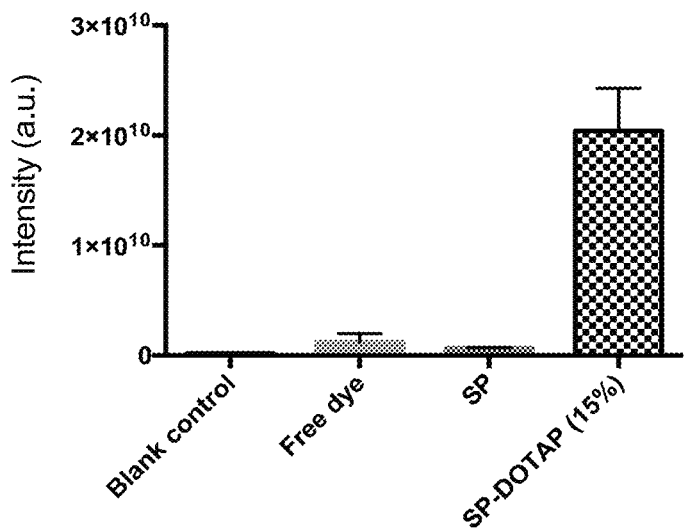
FIG. 14 is a bar graph showing the fluorescence intensity (arbitrary unit, A.U.) of cartilage explants after a 24-hour incubation with different samples, followed by washes and surface removal of remaining samples. The samples included (1) hydrogel formed by co-self assembly of SP and DOTAP, at 85% and 15% by weight, respectively, encapsulating a fluorescent dye; (2) hydrogel formed by self-assembled SP, encapsulating a fluorescent dye; and (3) the fluorescent dye. Blank control refers to the cartilage itself.

FIG. 14 shows adding DOTAP to SP hydrogel resulted in a significant increase in cartilage penetration compared to SP-only hydrogel.

Example 6: Co-Self Assembly of DOTMA with GRAS Ampihiphiles to Prepare Cartilage-Targeting Hydrogels DOTMA: 1,2-di-O-octadecenyl-3-trimethylammonium propane (Chloride Salt)

Methods

A GRAS amphiphile (80 mg) and DOTMA (20 mg) were weighed into a scintillation vial. The GRAS amphiphile in this Example includes triglycerol monostearate (TG18) or sucrose palmitate (SP). The mixture in the presence of 1 ml water-DMSO (4:1 volume ratio) was heated until it dissolved. The solution was allowed to cool down to room temperature on a flat and stable surface. Gelation was complete when no gravitational flow was observed upon inversion of the vial. Gelation was observed for all the GRAS amphiphile-DOTMA combinations and required 15-45 minutes. To prepare gels for adhesion experiments, a fluorescent dye, DiR, was encapsulated within the gel. Specifically, 40 μl DiR solution (2.5 mg/ml) in DMSO was added during the gel preparation process.

For adhesion assay, 50 μl hydrogel was applied to bovine cartilage explant (6 mm in diameter) and incubated at 37° C. for 1 hour. After 1 hour, cartilage explants were washed twice with PBS and imaged using in vivo imaging system (IVIS). Hydrogels either with or without DOTMA were evaluated. Hydrogels without DOTMA were prepared using similar method using 100 mg of the GRAS amphiphile without using DOTMA. Untreated cartilage (blank control) and cartilage treated with free dye were used as control.

Results

Figure 15:
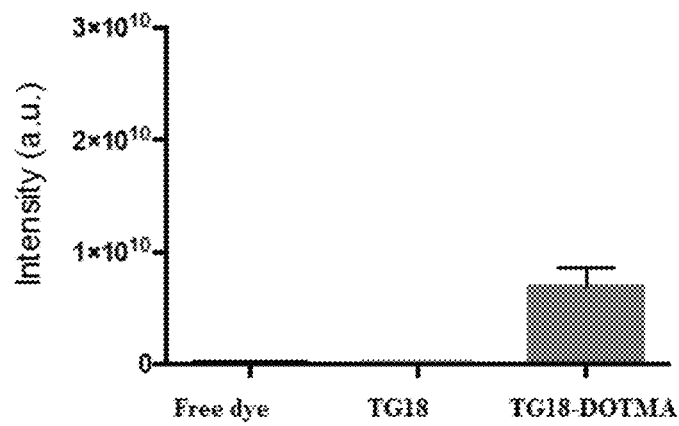
FIG. 15 is a bar graph showing the fluorescence intensity (arbitrary unit, A.U.) of cartilage explants following a 1-hour incubation with (1) hydrogel formed by co-self assembly of TG18 and DOTMA, at 80% and 20% by weight, respectively, encapsulating a fluorescent dye; (2) hydrogel formed by self assembly of TG18 alone, encapsulating a fluorescent dye; or (3) the fluorescent dye.

FIG. 15 shows co-self assembly of DOTMA with TG18 resulted in remarkable increase in adhesion to cartilage compared to TG18-only hydrogel.

Figure 16:
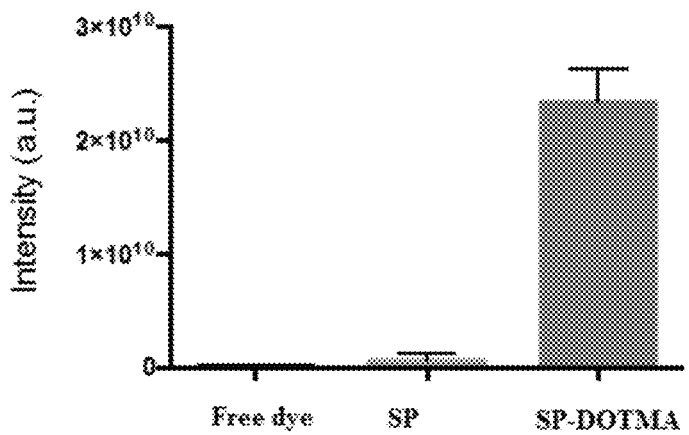
FIG. 16 is a bar graph showing the fluorescence intensity (arbitrary unit, A.U.) of cartilage explants following a 1-hour incubation with (1) hydrogel formed by co-self assembly of SP and DOTMA, at 80% and 20% by weight, respectively, encapsulating a fluorescent dye; (2) hydrogel formed by self assembly of SP alone, encapsulating a fluorescent dye; or (3) the fluorescent dye.

FIG. 16 shows co-self assembly of DOTMA with SP resulted in remarkable increase in adhesion to cartilage compared to SP-only hydrogel.

SP-DOTMA showed higher cartilage adhesion than TG18-DOTMA (Table 2). Higher adhesion to cartilage seen in SP-DOTMA, compared to TG18-DOTMA, may be due to more hydrophilicity of SP compared to TG18. Similar trend was observed with DOTAP-included gels as shown in Example 3.

TABLE 2

Comparison of hydrophilicity of GRAS amphiphiles and mean radiant intensity from the cartilage surface after incubation with co-self assembled gels between a GRAS amphiphile and DOTMA.

| GRAS amphiphile | Log P | Mean radiant intensity from the cartilage surface ($\times 10^{10}$) |
|---|---|---|
| SP | 0.64 | 2.34 |
| TG18 | 3.899 | 0.69 |

Example 7. Coating of Low Molecular Weight Chitosan (a Cationic Polysaccharide) on Sucrose Palmitate Gels Imparts Adhesion Capability to Cartilage Methods 100 mg sucrose palmitate (SP) was weighed into a scintillation vial. Chitosan was dissolved in water containing 1% acetic acid. Solutions containing different concentrations of chitosan (1 mg/ml, 0.5 mg/ml, and 0.1 mg/ml) were prepared. SP in the presence of 1 mL of chitosan solution-DMSO (4:1 volume ratio) was heated until dissolution; therefore forming a final/overall chitosan concentration of 0.8 mg/mL, 0.4 mg/mL, and 0.08 mg/mL, respectively. The solution was allowed to cool down to room temperature on a flat and stable surface.

Gelation was complete when no gravitational flow was observed upon inversion of the vial, and generally required 15-45 minutes.

To prepare gels for adhesion experiments, a fluorescent dye, DiR was encapsulated within the gel. Specifically, 40 μl DiR solution (2.5 mg/ml) in DMSO was added during the gel preparation process.

Gels with different chitosan solutions is referred to as: SP-chitosan (0.8 mg/ml), SP-chitosan (0.4 mg/ml) and SP-chitosan (0.08 mg/ml). The concentration refers to the final concentration of chitosan in the gels.

For adhesion assay, 50 μl SP gel or SP-chitosan gel was applied to bovine cartilage explant (6 mm in diameter) and incubated at 37 degree C. for 1 hour. After 1 hour, cartilage explants were washed twice with PBS and imaged using in vivo imaging system (IVIS). Hydrogels either with or without chitosan were evaluated. Untreated cartilage (blank control) and cartilage treated with free dye were used as control.

Results

Figure 17:
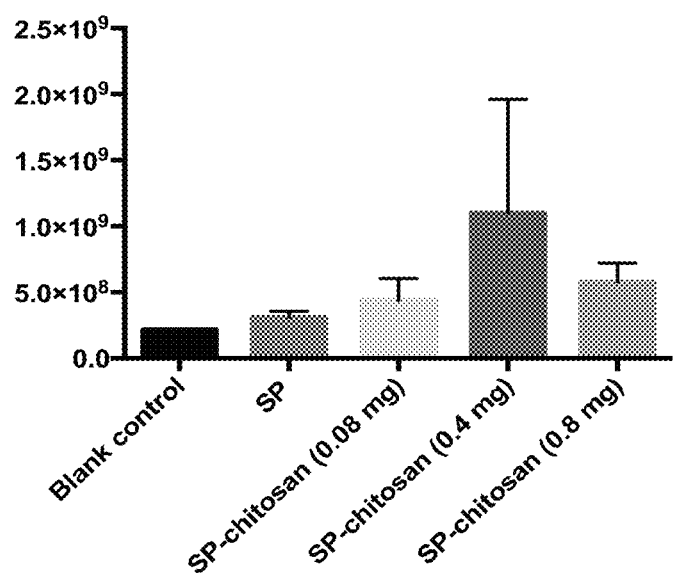
FIG. 17 is a bar graph showing the fluorescence intensity (arbitrary unit, A.U.) of cartilage explants following a 1-hour incubation with (1) hydrogel formed from 100 mg SP in a 1 mL-liquid medium containing 0.8 mg/mL chitosan, encapsulating a fluorescent dye; (2) hydrogel formed from 100 mg SP in a 1 mL-liquid medium containing 0.4 mg/mL chitosan, encapsulating a fluorescent dye; (3) hydrogel formed from 100 mg SP in a 1 mL-liquid medium containing 0.08 mg/mL chitosan, encapsulating a fluorescent dye; or (4) hydrogel formed from 100 mg SP in a 1 mL-liquid medium without chitosan.

FIG. 17 shows adding chitosan to SP hydrogel resulted in significant increase in adhesion to cartilage compared to only SP hydrogel. Greater than 0.08 mg/ml chitosan in sucrose palmitate gel was required for cartilage targeting.

We claim:

1. A gel composition which can adhere to cartilage tissue, the gel composition comprising an amphiphilic gelator having a molecular weight of less than 2,500 Da and a cationic agent,
   wherein the gelator is an enzyme-cleavable, generally recognized as safe (GRAS) compound selected from the group consisting of ascorbyl alkanoate, sorbitan alkanoate, triglycerol monoalkanoate, sucrose alkanoate, glycocholic acid, retinyl acetate, and alpha-tocopherol acetate, and combinations thereof,
   wherein the cationic agent is selected from the group consisting of cationic polysaccharides, 1,2-dioleoyl-3-trimethylammonium propane (DOTAP), 1,2-dioleyloxy-3-trimethylammonium propane chloride (DOTMA), polylysine, and combinations thereof,
   wherein the cationic agent is present in an amount greater than 5% by dry weight in a combined mass of the amphiphilic gelator having a molecular weight of less than 2,500 Da and the cationic agent or wherein the cationic agent is present in an amount of at least 0.08 mg/mL of the gel composition,
   wherein the gelator and the cationic agent co-self assemble or associate to form a homogeneous gel after heating to dissolution and cooling to room temperature, wherein the homogeneous gel is stable to inversion at a temperature between room and body temperature, and
   wherein the cationic agent electrostatically interacts or associates with one or more components of cartilage to enhance adhesion of the homogeneous gel to the cartilage, compared to a control gel composition lacking the cationic agent.

2. The gel composition of claim 1, wherein the cationic agent is present in an amount greater than 10% by dry weight in a combined mass of the amphiphilic gelator having a molecular weight of less than 2,500 Da and the cationic agent.

3. The gel composition of claim 1, wherein the gelator, the cationic agent, or both are compounds meeting the requirements of the U.S. Food and Drug Administration as generally recognized as safe (GRAS) compounds.

4. The gel composition of claim 1, wherein the gelator is an enzyme-cleavable, generally recognized as safe (GRAS) compound selected from the group consisting of ascorbyl alkanoate, sorbitan alkanoate, triglycerol monoalkanoate, sucrose alkanoate, glycocholic acid, and combinations thereof.

5. The gel composition of claim 4, wherein the gelator is selected from the group consisting of ascorbyl palmitate, triglycerol monostearate, sucrose palmitate, and sucrose stearate.

6. The gel composition of claim 1 further comprising one or more therapeutic, prophylactic, or diagnostic agents.

7. The gel composition of claim 6, wherein the one or more therapeutic, prophylactic, or diagnostic agents are released at less than. 10, 15, 20, 25, or 30% from the homogeneous gel when incubated in phosphate buffered saline at 37° C. for seven days.

8. The gel composition of claim 7, wherein the one or more therapeutic, prophylactic, or diagnostic agents are selected from the group consisting of immunomodulatory agents, chemotherapeutics, analgesics, anesthetics, joint lubricants, anti-pyretic agents, anti-infectious agents, tissue and/or bone regeneration promoters, vitamin, antioxidants, protease inhibitors and small interfering RNA.

9. The gel composition of claim 8 comprising immunomodulatory agents selected from the group consisting of steroids and non-steroidal anti-inflammatories.

10. The gel composition of claim 8 wherein the agent is selected from the group consisting of bone morphogenetic protein, transforming growth factor beta, fibroblast growth factor, stromal cell-derived factor 1 (SDF1), matrix metalloproteinase (MMP) inhibitor, Cathepsin-K inhibitor, and cysteine proteinase inhibitor, and platelet rich plasma.

11. The gel composition of claim 10 comprising Cathepsin-K inhibitors selected from the group consisting of balicatib (AAE581), relacatib (SB-462795), odanacatibe (MK-0822), MV061194, MV061748, MV061940, MV061645, MSX-081, LL-006235, and bicyclic ketone.

12. The gel composition of claim 10 comprising MMP inhibitors selected from the group consisting of CL-82198, actinonin, PD166793, CP 471474, WAY 170523, and ageladine A.

13. The gel composition of claim 10 comprising pain relief agents selected from the group consisting of lidocaine, procaine, tetracaine, dibucaine, and salts thereof.

14. The gel composition of claim 6, wherein the gel composition is free of solvent or the one or more therapeutic, prophylactic, or diagnostic agents which are unencapsulated within the homogeneous gel are removed.

15. The gel composition of claim 1 comprising two or more agents, wherein at least one agent potentiates efficacy of the one or more remaining agents.

16. A dosage unit kit, wherein the dosage unit comprises one or more containers for dry components comprising the amphiphilic gelator and the cationic agent and one or more containers for liquid components comprising one or more solvents, wherein the one or more containers for the dry and liquid components when mixed together form the self-assembled gel composition of claim 1.

17. A composition comprising the gel of claim 1 dispersed or broken up particles that are injectable through a needle when suspended in a carrier.

18. The gel composition of claim 1 wherein solvent is removed by lyophilization, drying or centrifugation.

19. The gel composition of claim 1, wherein the gel composition has an elastic modulus of from 10 to 10,000 Pascal and a viscous modulus of from 10 to 10,000 Pascal.

20. The gel composition of claim 1, wherein the cationic agent is present in an amount greater than 5% by dry weight in a combined mass of the amphiphilic gelator having a molecular weight of less than 2,500 Da and the cationic agent.

21. The gel composition of claim 1, wherein the cationic agent is present in an amount of at least 0.08 mg/mL of the gel composition.

22. A method of preparing a self-assembled gel composition adherent to cartilage tissue, comprising:
 combining one or more low molecular weight amphiphilic gelators of less than 2.500 Da, one or more cationic agents, and optionally a therapeutic, prophylactic, or diagnostic agent, to form an organo or hydrogel,
 wherein the cationic agent is greater than 10% by weight in a combined mass of the amphiphilic gelator having a molecular weight of less than 2,500 Da and the cationic agent, or is at least 0.08 mg/mL of the self-assembled gel composition.

23. The method of claim 22 wherein the gel composition is homogenized or sonicated to break up the gel into particles which retain the fibrous nanostructures formed in the gel.

* * * * *